(12) United States Patent
Schulze zur Wiesche et al.

(10) Patent No.: US 6,858,216 B2
(45) Date of Patent: Feb. 22, 2005

(54) COSMETIC AGENT CONTAINING 2-FURANONE DERIVATIVES

(75) Inventors: Erik Schulze zur Wiesche, Hamburg (DE); Detlef Hollenberg, Erkrath (DE); Britta Bossmann, Erkrath (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 10/289,061

(22) Filed: Nov. 6, 2002

(65) Prior Publication Data

US 2003/0206933 A1 Nov. 6, 2003

Related U.S. Application Data

(63) Continuation of application No. PCT/EP01/04822, filed on Apr. 28, 2001.

(30) Foreign Application Priority Data

May 6, 2000 (DE) .......................................... 100 22 077

(51) Int. Cl.$^7$ .......................... A61K 7/00; A61K 47/30
(52) U.S. Cl. .................. 424/401; 424/400; 514/772.2
(58) Field of Search ................................ 424/400, 401; 514/772.2

(56) References Cited

U.S. PATENT DOCUMENTS

| | | | |
|---|---|---|---|
| 4,237,253 A | 12/1980 | Jacquet et al. | |
| 4,393,886 A | 7/1983 | Strasilla et al. | |
| 4,420,622 A | 12/1983 | van de Moesdijk et al. | |
| 4,583,986 A | 4/1986 | Lapidus | |
| 4,672,078 A | 6/1987 | Sakai et al. | |
| 4,804,486 A | 2/1989 | Day | |
| 4,814,101 A | 3/1989 | Schieferstein et al. | |
| 4,865,774 A | 9/1989 | Fabry et al. | |
| 4,931,218 A | 6/1990 | Schenker et al. | |
| 5,151,304 A | 9/1992 | Lee | |
| 5,294,726 A | 3/1994 | Behler et al. | |
| 5,312,932 A | 5/1994 | Behler et al. | |
| 5,322,957 A | 6/1994 | Fabry et al. | |
| 5,484,531 A | 1/1996 | Kuehne et al. | |
| 5,534,267 A | 7/1996 | Neunhoeffer et al. | |
| 5,618,850 A * | 4/1997 | Coury et al. ............. | 514/772.2 |
| 5,773,595 A | 6/1998 | Weuthen et al. | |
| 5,831,080 A | 11/1998 | Sejpka et al. | |

FOREIGN PATENT DOCUMENTS

| | | |
|---|---|---|
| CA | 2 066 226 | 3/1991 |
| DE | 28 17 369 A1 | 10/1978 |
| DE | 37 23 354 A1 | 1/1989 |
| DE | 37 25 030 A1 | 2/1989 |
| DE | 39 26 344 A1 | 2/1991 |
| DE | 39 29 973 A1 | 3/1991 |
| DE | 40 27 241 A1 | 7/1991 |
| DE | 42 04 700 A1 | 8/1993 |
| DE | 195 03 456 C1 | 11/1995 |
| DE | 44 40 625 A1 | 5/1996 |
| DE | 44 13 686 C2 | 10/1996 |
| DE | 197 38 866 A1 | 3/1999 |
| DE | 197 56 454 C1 | 6/1999 |
| EP | 0 047 714 B1 | 10/1985 |
| EP | 0 175 074 | 3/1986 |
| EP | 0 217 274 A2 | 4/1987 |
| EP | 0 283 817 B1 | 12/1990 |
| EP | 0 466 986 B1 | 4/1994 |
| EP | 0 561 825 B1 | 9/1995 |
| EP | 0 561 999 B1 | 1/1996 |
| EP | 0 612 759 B1 | 10/1996 |
| EP | 0 740 741 B2 | 11/1996 |
| GB | 2 104 091 A | 3/1983 |
| GB | 2 235 451 A | 3/1991 |
| JP | 04-091084 | 3/1992 |
| JP | 07-126148 | 5/1995 |
| JP | 07-242526 | 9/1995 |
| JP | 08-026942 | 1/1996 |
| JP | 11-292753 | 10/1999 |
| WO | WO 92/13829 A1 | 8/1992 |
| WO | WO 94/08970 A1 | 4/1994 |

OTHER PUBLICATIONS

Database accession No. 131:303228 CA XP002185854 (JP 11 292753 Oct. 26, 1999).

Database accession No. 124:269960 CA XP002185855 (JP 08 026942 Jan. 30, 1996).

Database accession No. 124:66215 CA XP 002185856 (JP 07 242526 Sep. 19, 1995).

Database accession No. 123:122753 CA XP002185857 (JP 07 126148 May 16, 1996).

Database accession No. 1992–147994 XP002185858 (JP 04 091084 Mar. 24, 1992).

International Cosmetic Ingredient Dictionary and Handbook, 7th Edition, 1997, (cover page and table of contents).

A.K. Biswas et al., "Surface–Active Properties of Sodium Salts of Sulfated Fatty Acid Monoglycerides", Journal of the American Oil Chemists Society, vol. 37, pp. 171–175 (1960).

F. U. Ahmed, "Efficient synthesis of Fatty Monoglyceride Sulfates from Fatty Acids and Fatty Acid Methyl Esters", Journal of the American Oil Chemists Society, vol. 67, pp. 8–14 (1990).

Falbe et al., Rompp–Lexikon Chemis, vol. 10, Georg thieme Verlag Stuttgart, N York, pp. 1764 (1997).

Introduction to the Ingredient Declaration of Cosmetic Producs, published by the Industrieverband Korperpflege– und Waschmittel elV. (IKW) Frankfurt, 3rd Edition, p. 44.

Schrader, Grundlagen und Rezepturen der Kosmetika, vol. 2, Huthig Buch Vergla Heidelberg, (1989).

(List continued on next page.)

Primary Examiner—Shelley A. Dodson
(74) Attorney, Agent, or Firm—Stephen D. Harper; Glenn E. J. Murphy; Gregory M. Hill

(57) ABSTRACT

There is provided cosmetic agents containing 2-furanone derivatives for the treatment of skin and hair.

17 Claims, No Drawings

OTHER PUBLICATIONS

Kahlweit et al., "Phasenverhalten ternarer Systeme des Typs $H_2O$ –O1–nichtionisches Amphiphil", Angewandte Chemie vol. 97, pp. 655–669 (1985).

Forster et al., "Influence of Microemulsion Phases on the Preparation of Fine–Disperse Emulsions", Advances in Colloid and Interface Sciences, vol. 58, pp. 119–149 (1995).

Charles Zviak, "Hair Coloring", The Science of Hair Care, Chapter 7, vol. 7, Dermatology, Marcel Dekker Inc., pp. 248–250 (1986).

Charles Zviak, "Oxidation Coloring", The Science of Hair Care, Chapter 8, vol. 7, Dermatology, Marcel Dekker Inc., pp. 264–267 (1986).

* cited by examiner

COSMETIC AGENT CONTAINING 2-FURANONE DERIVATIVES

CROSS REFERENCE TO RELATED APPLICATIONS

This application is a continuation under 35 U.S.C. §365 (c) and §120 of International Application No. PCT/EP01/04822 filed Apr. 28, 2001 and under §119 of German Application No. 100 22 077.0 filed May 6, 2000.

SUMMARY OF THE INVENTION

The invention relates to cosmetic agents containing certain derivatives of 2-furanone, and to the use of these agents for the treatment of keratin fibers and skin.

BACKGROUND OF THE INVENTION

Cosmetic agents for caring for and maintaining the natural functions of the skin and hair are becoming more and more important. This is due, inter alia, to the changed consumer habits and fashion trends. Thus, for example as a result of the intensive utilization of tanning studios, the structure of skin and hair is permanently damaged to a greater extent by UV light. This damage is evident on the skin, like on the hair, for example from a loss in elasticity.

In addition, extensive physical activity outdoors leads to frequent intensive cleaning of skin and hair. As a result, the protective film of sebum, which is produced continuously by the numerous sebaceous glands, or else the sebum production of the sebaceous glands itself may be considerably impaired. This results in greasy skin and greasy hair.

Fashion trends with current colors for "make-up", lipsticks for coloring the lips and mascara, and also hair colorants and waving agents contribute, in the case of stressed skin and predamaged hair, to further impairment of the natural state of skin and hair. It is therefore not surprising that the number of consumers with sensitive, less elastic, rough and irritable skin, and hair which is impaired with regard to combability, shine, elasticity, brittleness and maximum breaking force is increasing considerably.

There has therefore been no lack of attempts to overcome these inadequacies. In this regard, skincare emulsions have, inter alia, been further optimized with regard to their irritancy potential through the choice of suitable emulsifiers. For the cleaning of skin and hair, use is made of mild surfactants in order not to additionally burden skin and hair. Refatting substances have been used to try to avoid stimulating sebum production during cleaning. UV protectants and vitamins, such as, for example, vitamin E, are said to alleviate the disadvantageous effects of UV light. Protein hydrolyzates are used for correcting the internal structure of skin and hair. Plant and algae extracts can be used, for example, to influence the moisture level in skin and hair.

In addition, cosmetic active ingredients are being increasingly used in agents for cleaning and caring for surfaces such as glass, porcelain, leather, textiles, floors of all types in the home and commercially in order not to additionally burden the skin of the user of such products. For example, hand dishwashing detergents with care additives such as proteins or refatting substances are commercially available.

However, there is still a need for agents which are characterized by a reduction in the undesired damage to skin and hair. It has now been found that the use of derivatives of 2-furanone as active ingredient in cosmetic agents leads to surprisingly good properties of the treated skin and of the hair, in particular to improved combabilities, to improved shine and to improved elasticity.

DESCRIPTION OF THE INVENTION

The invention firstly therefore provides a cosmetic agent containing customary cosmetic constituents, characterized in that it contains, as active ingredient, a 2-furanone of the formula (I) and/or of the formula (II),

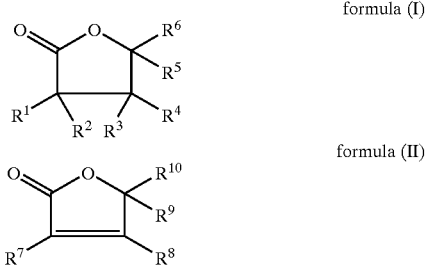

formula (I)

formula (II)

in which the radicals $R^1$ to $R^{10}$, independently of one another, represent:

hydrogen, —OH, a methyl, methoxy, aminomethyl or hydroxymethyl radical

—$C_2$–$C_4$-saturated or mono- or diunsaturated, branched or linear hydrocarbon radical, —$C_2$–$C_4$-saturated or mono- or diunsaturated, branched or linear mono-, di- or trihydroxy hydrocarbon radical, —$C_2$–$C_4$-saturated or mono- or diunsaturated, branched or linear mono-, di- or triamino hydrocarbon radical, a group —$OR^{11}$, where $R^{11}$ is a —$C_2$–$C_4$-saturated or mono- or diunsaturated, branched or linear hydrocarbon radical, —$C_2$–$C_4$-saturated or mono- or diunsaturated, branched or linear mono-, di- or trihydroxy hydrocarbon radical, a group —$NR^{12}R^{13}$, where $R_{12}$ and $R_{13}$, in each case independently of one another, are hydrogen, a methyl, a —$C_2$–$C_4$-saturated or mono- or diunsaturated, branched or linear hydrocarbon radical, a —$C_2$–$C_4$-saturated or mono- or diunsaturated, branched or linear mono-, di- or trihydroxy hydrocarbon radical, a group —$COOR^{14}$, where $R^{14}$ is hydrogen, a methyl, a —$C_2$–$C_4$-saturated or mono- or diunsaturated, branched or linear hydrocarbon radical, a —$C_2$–$C_4$-saturated mono- or diunsaturated, branched or linear mono-, di- or trihydroxy hydrocarbon radical, a —$C_2$–$C_4$-saturated or mono- or diunsaturated, branched or linear mono-, di- or triamino hydrocarbon radical, a group —$CONR^{15}R^{16}$, where $R^{15}$ and $R^{16}$ are in each case hydrogen, methyl, a —$C_2$–$C_4$-saturated or mono- or diunsaturated, branched or linear hydrocarbon radical, a —$C_2$–$C_4$-saturated mono- or diunsaturated, branched or linear mono-, di- or trihydroxy hydrocarbon radical, a —$C_2$–$C_4$-saturated or mono- or diunsaturated, branched or linear mono-, di- or triamino hydrocarbon radical, a group —$COR^{16}$, where $R^{16}$ is a methyl, a —$C_2$–$C_4$-saturated or mono- or diunsaturated, branched or linear hydrocarbon radical, a —$C_2$–$C_4$-saturated or mono- or diunsaturated, branched or linear mono-, di- or trihydroxy hydrocarbon radical, a —$C_2$–$C_4$-saturated or mono- or diunsaturated, branched or linear mono-, di- or triamino hydrocarbon radical, a group —$OCOR^{17}$, where $R^{17}$ is a methyl, a —$C_2$–$C_{30}$-saturated or mono- or polyunsaturated, branched or linear hydrocarbon radical, a —$C_2$–$C_{30}$-saturated or mono- or polyunsaturated, branched or linear mono-, di-, tri- or polyhydroxy hydrocarbon radical, a $—C_2–C_{30}$-saturated or mono- or polyunsaturated, branched or linear mono-, di-, tri- or polyamino hydrocarbon radical, with the proviso that for the case when $R^7$ and $R^8$ are —OH and at the same time $R^9$ or $R^{10}$ are hydrogen, the remaining group $R^9$ or $R^{10}$ is not a dihydroxyethyl radical.

2-Furanones are known compounds and are described, for example, in "Römppy's Lexicon of Chemistry, Interactive CD-Rom Version 2.0, using the keyword "dihydro-3-hydroxy-4,4-dimethtyl-2(3H)-furanone", and in "Ullmann's Encyclopedia, sixth edition 1999, electronic release" in Sections 2.4, 2.7, 3.2, 3.4, 4.3, 6, 11 and 15 and the specifications cited therein with regard to the preparation and use. Reference is expressly made to these chapters and the literature cited therein. The compounds of the formulae (I) and (II) are used as intermediates in the synthesis of natural substances, and also in the preparation of medicaments and vitamins. The preparation of the active ingredients according to the formulae (I) and (II) can be carried out, for example, by reacting primary alcohols with acrylic acids. In addition, compounds of the formula (I) are obtained by reactions starting from hydroxypivaldehyde. Similarly, carbonylations of alkynes lead to substituted 2-furanones of the formula (I) or (II). Finally, the compounds of the formula (I) or of the formula (II) can be obtained by intramolecular esterification of the corresponding hydroxycarboxylic acids. For example, the following compounds are obtained by one of the synthesis routes listed above: 2,5-dihydro-5-methoxy-2-furanone, tetrahydro-5-oxo-2-furanecarboxylic acid, dihydro-3-hydroxy-4,4-dimethyl-2(3H)-furanone, or 3,4-dimethyl-5-pentylidenedihydro-2(5H)-furanone or 4-hydroxy-2,5-dimethyl-3(2H)-furanone. The 2-furanones according to the invention of course include all possible stereoisomers, and also mixtures thereof. The 2-furanones according to the invention do not permanently affect the odor of the cosmetic agents such that perfuming of the agents has to be carried out separately.

Preferred compounds of the formula (I) and/or of the formula (II) may be compounds in which the substituents $R^1$, $R^2$ and $R^7$, independently of one another, represent:

hydrogen, an —OH, a methyl, methoxy, aminomethyl, hydroxymethyl radical, a $—C_2–C_4$-saturated or mono- or diunsaturated, branched or linear mono-, di- or trihydroxy hydrocarbon radical, a $—C_2–C_4$-saturated or mono- or diunsaturated, branched or linear mono-, di- or triamino hydrocarbon radical, a group $—OR^{11}$, where $R^{11}$ is a $—C_2–C_4$-saturated or mono- or diunsaturated, branched or linear hydrocarbon radical, $—C_2–C_4$-saturated or mono- or diunsaturated, branched or linear mono-, di- or trihydroxy hydrocarbon radical, a group $—NR^{12}R^{13}$, where $R^{12}$ and $R^{13}$, in each case independently of one another, are hydrogen, a methyl, a $—C_2–C_4$-saturated or mono- or diunsaturated, branched or linear hydrocarbon radical, a $—C_2–C_4$-saturated or mono- or diunsaturated, branched or linear mono-, di- or trihydroxy hydrocarbon radical, a group $—COOR^{14}$, where $R^{14}$ is hydrogen, a methyl, a $—C_2–C_4$-saturated or mono- or diunsaturated, branched or linear hydrocarbon radical, a $—C_2–C_4$-saturated or mono- or diunsaturated, branched or linear mono-, di- or trihydroxy hydrocarbon radical, a $C_2–C_4$-saturated or mono- or diunsaturated, branched or linear mono-, di- or triamino hydrocarbon radical, a group $—COR^{16}$, where $R^{16}$ is a methyl, a $—C_2–C_4$-saturated or mono- or diunsaturated, branched or linear hydrocarbon radical, a $—C_2–C_4$-saturated or mono- or diunsaturated, branched or linear mono-, di- or trihydroxy hydrocarbon radical, a $—C_2–C_4$-saturated or mono- or diunsaturated, branched or linear mono-, di- or triamino hydrocarbon radical, a group $—OCOR^{17}$, where $R^{17}$ is a methyl, a $—C_2–C_{30}$-saturated or mono- or polyunsaturated, branched or linear hydrocarbon radical, a $—C_2–C_{30}$-saturated or mono- or polyunsaturated, branched or linear mono-, di-, tri- or polyhydroxyalkyl radical, or a $—C_2–C_{30}$-saturated or mono- or polyunsaturated, branched or linear mono-, di-, tri- or polyamino hydrocarbon radical.

In a further embodiment of the teaching according to the invention, it has been found that in the compounds of the formula (I) or of the formula (II), the radicals $R^3$, $R^4$ and $R^8$ preferably independently of one another represent:

hydrogen, an —OH, a methyl, methoxy, aminomethyl, hydroxymethyl radical, a $—C_2–C_4$-saturated or mono- or diunsaturated, branched or linear hydrocarbon radical, a $—C_2–C_4$-saturated or mono- or diunsaturated, branched or linear mono-, di- or trihydroxy hydrocarbon radical or a $—C_2–C_4$-saturated or mono- or diunsaturated, branched or linear mono-, di- or triamino hydrocarbon radical.

In addition, it may be preferred if in the novel active ingredient according to formula (I) and/or formula (II), for the radicals $R^5$, $R^6$, $R^9$ and $R^{10}$, independently of one another, represent:

hydrogen, a —OH, a methyl, methoxy, aminomethyl, hydroxymethyl radical, a $—C_2–C_4$-saturated or mono- or diunsaturated, branched or linear hydrocarbon radical, a $—C_2–C_4$-saturated or mono- or diunsaturated, branched or linear mono-, di- or trihydroxy hydrocarbon radical or a $—C_2–C_4$-saturated or mono- or diunsaturated, branched or linear mono-, di- or triamino hydrocarbon radical.

In a particularly preferred embodiment of the teaching according to the invention, a compound of the formula (I) is used. In this connection, it may be preferred that, in a compound of the formula (I), the radicals $R^1$ and $R^2$, independently of one another, represent:

hydrogen, an —OH, a methyl, methoxy, aminomethyl, hydroxymethyl radical, a $—C_2–C_4$-saturated or mono- or diunsaturated, branched or linear mono-, di- or trihydroxy hydrocarbon radical, a group $—OR^{11}$, where $R^{11}$ is a $—C_2–C_4$-saturated or mono- or diunsaturated, branched or linear hydrocarbon radical, $—C_2–C_4$-saturated or mono- or diunsaturated, branched or linear mono-, di- or trihydroxy hydrocarbon radical, a group $—COOR^4$, where $R^{14}$ is hydrogen, a methyl, a $—C_2–C_4$-saturated or mono- or diunsaturated, branched or linear hydrocarbon radical, a $—C_2–C_4$-saturated mono- or diunsaturated, branched or linear mono-, di- or trihydroxy hydrocarbon radical, a group $—COR^{14}$, where $R^{14}$ is a methyl, a $—C_2–C_4$-saturated or mono- or diunsaturated, branched or linear hydrocarbon radical, a $—C_2–C_4$-saturated or mono- or diunsaturated, branched or linear mono-, di- or trihydroxy hydrocarbon radical, a group —OCOR$^{17}$, where R$^{17}$ is a methyl, a —C$_2$–C$_{30}$-saturated or mono- or polyunsaturated, branched or linear hydrocarbon radical, a —C$_2$–C$_{30}$-saturated or mono- or polyunsaturated, branched or linear mono-, di-, tri- or polyhydroxy hydrocarbon radical.

In addition, in this particularly preferred embodiment of the teaching according to the invention, it may be advantageous if, in the compounds of the formula (I), the radicals R$^3$ and R$^4$, independently of one another, represent:

hydrogen, an —OH, a methyl, methoxy, aminomethyl, hydroxymethyl radical, a —C$_2$–C$_4$-saturated or mono- or diunsaturated, branched or linear mono-, di- or trihydroxy hydrocarbon radical, a group —OR$^{11}$, where R$^{11}$ is a —C$_2$–C$_4$-saturated or mono- or diunsaturated, branched or linear hydrocarbon radical, —C$_2$–C$_4$-saturated or mono- or diunsaturated, branched or linear mono-, di- or trihydroxy hydrocarbon radical, a group —COOR$^{14}$, where R$^{14}$ is hydrogen, a methyl, a —C$_2$–C$_4$-saturated or mono- or diunsaturated, branched or linear hydrocarbon radical, a —C$_2$–C$_4$-saturated mono- or diunsaturated, branched or linear mono-, di- or trihydroxy hydrocarbon radical, a group —OCOR$^{17}$, where R$^{17}$ is a methyl, a —C$_2$–C$_{30}$-saturated or mono- or polyunsaturated, branched or linear hydrocarbon radical, a —C$_2$–C$_{30}$-saturated or mono- or polyunsaturated, branched or linear mono-, di-, tri- and/or polyhydroxy hydrocarbon radical.

In this preferred embodiment, it may be further advantageous for the compounds according to formula (I) for the radicals R$^5$ and R$^6$, independently of one another, represent:

hydrogen, an —OH, a methyl, methoxy, aminomethyl, hydroxymethyl radical, a —C$_2$–C$_4$-saturated or mono- or diunsaturated, branched or linear mono-, di- or trihydroxy hydrocarbon radical, a group —OR$^{11}$, where R$^{11}$ is a —C$_2$–C$_4$-saturated or mono- or diunsaturated, branched or linear hydrocarbon radical, —C$_2$–C$_4$-saturated or mono- or diunsaturated, branched or linear mono-, di- or trihydroxy hydrocarbon radical.

In a very particularly preferred embodiment of the teaching according to the invention, the compound according to the formula (I) used is dihydro-3-hydroxy-4,4-dimethyl-2(3H)-furanone.

The active ingredient according to the invention is used in the cosmetic agents in amounts of from 0.001 to 10% by weight, based on the overall agent, preferably in amounts of from 0.01 to 5% by weight and very particularly preferably in amounts of from 0.05 to 3% by weight.

In a preferred embodiment of the teaching according to the invention, the effect can be further increased with polymers. Polymers is understood as meaning both natural and synthetic polymers, which may be anionic, cationic, amphoterically charged or nonionic.

Cationic polymers are understood as meaning polymers which have, in the main chain and/or side chain, a group which may be "temporarily" or "permanently" cationic. According to the invention, "permanently cationic" is used to refer to those polymers which have a cationic group irrespective of the pH of the agent. These are usually polymers which contain a quaternary nitrogen atom, for example in the form of an ammonium group. Preferred cationic groups are quaternary ammonium groups. In particular, those polymers in which the quaternary ammonium group are bonded via a C$_{1-4}$-hydrocarbon group to a polymer main chain constructed from acrylic acid, methacrylic acid or derivatives thereof have proven particularly suitable.

Homopolymers of the general formula (III),

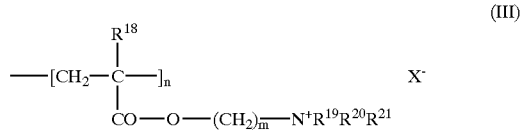

(III)

in which R$^{18}$=—H or —CH$_3$, R$^{19}$, R$^{20}$ and R$^{21}$, independently of one another, are chosen from C$_{1-4}$-alkyl, -alkenyl or hydroxyalkyl groups, m=1, 2, 3 or 4, n is a natural number and X$^-$ is a physiologically compatible organic or inorganic anion, and also copolymers consisting essentially of the monomer units listed in formula (III) and also nonionogenic monomer units are particularly preferred cationic polymers. Within the scope of these polymers, preference is given according to the invention to those for which at least one of the following conditions applies:

R$^{18}$ is a methyl group

R$^{19}$ R$^{20}$ and R$^{21}$ are methyl groups m has the value 2.

Suitable as physiologically compatible counterion X$^-$ are, for example, halide ions, sulfate ions, phosphate ions, methosulfate ions, and organic ions, such as lactate, citrate, tartrate and acetate ions. Preference is given to halide ions, in particular chloride.

A particularly suitable homopolymer is the, if desired crosslinked, poly(methacryloyloxyethyltrimethylammonium chloride) with the INCI name Polyquaternium-37. The crosslinking can if desired take place using polyolefinically unsaturated compounds, for example divinylbenzene, tetraallyloxyethane, methylenebisacrylamide, diallyl ether, polyallyl polyglyceryl ether, or allyl ethers of sugars or sugar derivatives, such as erythritol, pentaerythritol, arabitol, mannitol, sorbitol, sucrose or glucose. Methylenebisacrylamide is a preferred crosslinking agent.

The homopolymer is preferably used in the form of a nonaqueous polymer dispersion which should have a polymer content not below 30% by weight. Such polymer dispersions are available commercially under the names Salcare® SC 95 (about 50% polymer content, further components: Mineral Oil (INCI name) and tridecylpolyoxypropylene polyoxyethylene ether (INCI name: PPG-1 Trideceth-6)) and Salcare® SC 96 (about 50% polymer content, further components: mixture of diesters of propylene glycol with a mixture of caprylic and capric acid (INCI name: Propylene Glycol Dicaprylate/Dicaprate) and tridecylpolyoxypropylene polyoxyethylene ether (INCI name: PPG-1 Trideceth-6)).

Copolymers with monomer units according to formula (III) contain, as nonionogenic monomer units, preferably acrylamide, methacrylamide, acrylic C$_{1-4}$-alkyl esters and methacrylic C$_{1-4}$-alkyl esters. Of these nonionogenic monomers, the acrylamide is particularly preferred. As described above in the case of the homopolymers, these copolymers too may be crosslinked. A copolymer preferred according to the invention is the crosslinked acrylamide-methacryloyloxyethyltrimethylammonium chloride copolymer. Those copolymers in which the monomers are present in a weight ratio of about 20:80 are available commercially as about 50% strength nonaqueous polymer dispersion under the name Salcare® SC 92.

Further preferred cationic polymers are, for example, quaternized cellulose derivatives, as are available commercially under the names Celquat® and Polymer JR®.

The compounds Celquat® H 100, Celquat® L 200 and Polymer JR® 400 are preferred quaternized cellulose derivatives, cationic alkyl polyglycosides according to German patent DE 44 13 686, cationized honey, for example the commercial product Honeyquat® 50, cationic guar derivatives, such as, in particular, the products sold under the trade names Cosmedia® Guar and Jaguar®, polysiloxanes with quaternary groups, such as, for example, the commercially available products Q2-7224 (manufacturer: Dow Corning; a stabilized trimethylsilylamodimethicone), Dow Corning® 929 Emulsion (comprising a hydroxylamino-modified silicone, which is also referred to as Amodimethicone), SM-2059 (manufacturer: General Electric), SLM-55067 (manufacturer: Wacker) and Abil®-Quat 3270 and 3272 (manufacturer: Th. Goldschmidt; diquaternary polydimethylsiloxanes, Quaternium-80), polymeric dimethyldiallylammonium salts and copolymers thereof with esters and amides of acrylic acid and methacrylic acid. The products available commercially under the names Merquat®100 (poly(dimethyldiallylammonium chloride)) and Merquat®550 (dimethyldiallylammonium chloride-acrylamide copolymer) are examples of such cationic polymers, copolymers of vinylpyrrolidone with quaternized derivatives of the dialkylaminoalkyl acrylate and methacrylate, such as, for example, vinylpyrrolidone-dimethylaminoethyl methacrylate copolymers quaternized with diethyl sulfate. Such compounds are available commercially under the names Gafquat®734 and Gafquat®755, vinylpyrrolidone-vinylimidazolium methochloride copolymers, as are supplied under the names Luviquat® FC 370, FC 550, FC 905 and HM 552.

quaternized polyvinyl alcohol, and the polymers with quaternary nitrogen atoms in the polymer main chain known under the names Polyquaternium 2,
Polyquaternium 17,
Polyquaternium 18 and
Polyquaternium 27.

As cationic polymers, it is likewise possible to use the polymers known under the names Polyquaternium-24 (commercial product e.g. Quatrisoft® LM 200). According to the invention, it is likewise possible to use the copolymers of vinylpyrrolidone, as are available as commercial products Copolymer 845 (manufacturer: ISP), Gaffix® VC 713 (manufacturer: ISP), Gafquat® ASCP 1011, Gafquat®HS 110, Luviquat®8155 and Luviquat® MS 370.

Further cationic polymers according to the invention are the so-called "temporarily cationic" polymers. These polymers usually contain an amino group which, at certain pH values, is in the form of a quaternary ammonium group and thus cationic. Preference is given, for example, to chitosan and derivatives thereof, as are freely available commercially, for example, under the trade names Hydagen® CMF, Hydagen® HCMF, Kytamer® PC and Chitolam® NB/101. Chitosans are deacetylated chitins which are available commercially in varying degrees of deacetylation and varying degrees of degradation (molecular weights). Their preparation is described, for example in DE 44 40 625 A1 and DE 195 03 465 A1.

Particularly suitable chitosans have a degree of deacetylation of at least 80% and a molecular weight of $5 \cdot 10^5$ to $5 \cdot 10^6$ (g/mol).

For the preparation of preparations according to the invention, the chitosan must be converted into the salt form. This can be carried out by dissolution in dilute aqueous acids. Suitable acids are either mineral acids, such as, for example, hydrochloric acid, sulfuric acid and phosphoric acid, or organic acids, e.g. low molecular weight carboxylic acids, polycarboxylic acids and hydroxycarboxylic acids. It is also possible to use higher molecular weight alkylsulfonic acids or alkylsulfuric acids or organophosphoric acids, provided these have the required physiological compatibility. Suitable acids for converting the chitosan into the salt form are, for example, acetic acid, glycolic acid, tartaric acid, malic acid, citric acid, lactic acid, 2-pyrrolidinone-5-carboxylic acid, benzoic acid or salicyclic acid. Preference is given to using low molecular weight hydroxycarboxylic acids, such as, for example, glycolic acid or lactic acid.

The anionic polymers which can aid the action of the active ingredient according to the invention are an anionic polymers which have carboxylate and/or sulfonate groups. Examples of anionic monomers of which such polymers can consist are acrylic acid, methacrylic acid, crotonic acid, maleic anhydride and 2-acrylamido-2-methylpropanesulfonic acid. Here, the acidic groups may be completely or partially present as sodium, potassium, ammonium, mono- or triethanolammonium salt. Preferred monomers are 2-acrylamido-2-methylpropanesulfonic acid and acrylic acid.

Anionic polymers which have proven very particularly effective are those which contain, as the sole monomer or comonomer, 2-acrylamido-2-methylpropanesulfonic acid, where the sulfonic acid group can completely or partially be in the form of the sodium, potassium, ammonium, mono- or triethanolammonium salt.

Particular preference is given to the homopolymer of 2-acrylamido-2-methylpropanesulfonic acid, which is commercially available, for example, under the name Rheothik®11-80.

Within this embodiment, it may be preferred to use copolymers of at least one anionic monomer and at least one nonionogenic monomer. With regard to the anionic monomers, reference is made to the substances listed above. Preferred nonionogenic monomers are acrylamide, methacrylamide, acrylic esters, methacrylic esters, vinylpyrrolidone, vinyl ethers and vinyl esters.

Preferred anionic copolymers are acrylic acid-acrylamide copolymers and, in particular, polyacrylamide copolymers with sulfonic acid group-containing monomers. A particularly preferred anionic copolymer consists of 70 to 55 mol % of acrylamide and 30 to 45 mol % of 2-acrylamido-2-methylpropanesulfonic acid, where the sulfonic acid group is completely or partially in the form of the sodium, potassium, ammonium, mono- or triethanolammonium salt. This copolymer can also be in crosslinked form, where the crosslinking agents used are preferably polyolefinically unsaturated compounds such as tetraallyloxyethane, allylsucrose, allylpentaerythritol and methylenebisacrylamide. Such a polymer is present in the commercial product Sepigel®305 from SEPPIC. Use of this compound, which as well as comprising the polymer component comprises a hydrocarbon mixture ($C_{13}$–$C_{14}$-isoparaffin) and a nonionogenic emulsifier (Laureth-7), has proven particularly advantageous within the scope of the teaching according to the invention.

The sodium acryloyldimethyltaurate copolymers sold under the name Simulgel®600 as a compound with isohexadecane and polysorbate-80 have also proven particularly effective according to the invention.

Likewise preferred anionic homopolymers are uncrosslinked and crosslinked polyacrylic acids. Here, allyl ethers of pentaerythritol, of sucrose and of propylene may be preferred crosslinking agents. Such compounds are commercially available, for example, under the trade name Carbopol®.

Copolymers of maleic anhydride and methyl vinyl ether, in particular those with crosslinking, are likewise color-retaining polymers. A maleic acid-methyl vinyl ether copolymer crosslinked with 1,9-decadiene is commercially available under the name Stabileze® QM.

Further polymers which can [lacuna] used as a constituent for increasing the action of the active ingredient according to the invention are amphoteric polymers. The term amphoteric polymers covers both those polymers which have both free amino groups and also free —COOH or $SO_3H$ groups in the molecule and are capable of forming internal salts, and also zwitterionic polymers which contain quaternary ammonium groups and —COO$^-$ or —$SO_3^-$ groups in the molecule, and those polymers which contain —COOH or $SO_3H$ groups and quaternary ammonium groups.

One example of an amphopolymer which can be used according to the invention is the acrylic resin obtainable under the name Amphomer®, which represents a copolymer of tert-butylaminoethyl methacrylate, N-(1,1,3,3-tetramethylbutyl)acrylamide and two or more monomers from the group consisting of acrylic acid, methacrylic acid and simple esters thereof.

Further amphoteric polymers which can be used according to the invention are the compounds given in British laid-open specification 2 104 091, European laid-open specification 47 714, European laid-open specification 217 274, European laid-open specification 283 817 and German laid-open specification 28 17 369.

Amphoteric polymers which are preferably used are those polymers which are composed essentially of
(a) monomers with quaternary ammonium groups of the general formula (IV):

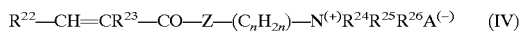

$$R^{22}-CH=CR^{23}-CO-Z-(C_nH_{2n})-N^{(+)}R^{24}R^{25}R^{26}A^{(-)} \quad (IV)$$

in which $R^{22}$ and $R^{23}$, independently of one another, are hydrogen or a methyl group, and $R^{24}$, $R^{25}$ and $R^{26}$, independently of one another, are alkyl groups having 1 to 4 carbon atoms, Z is an NH group or an oxygen atom, n is an integer from 2 to 5 and $A^{(-)}$ is the anion of an organic or inorganic acid and
(b) monomeric carboxylic acids of the general formula (V):

$$R^{27}-CH=CR^{28}-COOH \quad (V)$$

in which $R^{27}$ and $R^{28}$, independently of one another, are hydrogen or methyl groups.

These compounds can be used in accordance with the invention either directly or else in salt form, which is obtained by neutralization of the polymers, for example with an alkali metal hydroxide. With regard to the details of the preparation of these polymers, reference is made expressly to the content of German laid-open specification 39 29 973. Very particular preference is given to those polymers in which monomers of type (a) are used in which $R^{24}$, $R^{25}$ and $R^{26}$ are methyl groups, Z is an NH group and $A^{(-)}$ is a halide, methoxysulfate or ethoxysulfate ion; acrylamidopropyltrimethylammonium chloride is a particularly preferred monomer (a). The monomer (b) used for said polymers is preferably acrylic acid.

The agents according to the invention can, in a third variant, also comprise nonionogenic polymers.

Suitable nonionogenic polymers are, for example:

vinylpyrrolidone/vinyl ester copolymers, as are sold, for example, under the trade name Luviskol® (BASF). Luviskol® VA 64 and Luviskol® VA 73, each being vinylpyrrolidone/vinyl acetate copolymers, are likewise preferred nonionic polymers.

Cellulose ethers, such as hydroxypropylcellulose, hydroxyethylcellulose and methylhydroxypropylcellulose, as are sold, for example, under the trade names Culminal® and Benecel® (AQUALON)

Shellac

Polyvinylpyrrolidones, as are sold, for example, under the name Luviskol® (BASF).

Siloxanes. These siloxanes may either be water-soluble or water-insoluble. Both volatile and also nonvolatile siloxanes are suitable, nonvolatile siloxanes being understood as meaning those compounds whose boiling point at atmospheric pressure is above 200° C. Preferred siloxanes are polydialkylsiloxanes, such as, for example, polydimethylsiloxane, polyalkylarylsiloxanes, such as, for example, polyphenylmethylsiloxane, ethoxylated polydialkylsiloxanes and polydialkylsiloxanes which contain amine and/or hydroxy groups.

Glycosidically substituted silicones according to EP 0612759 B1.

It is also possible according to the invention for the preparations used to contain two or more, in particular two, different polymers of equal charge and/or in each case one ionic and one amphoteric and/or nonionic polymer.

According to the invention, the term polymer is likewise understood as meaning special preparations of polymers such as spherical polymer powders. Various methods are known for preparing such microspheres from various monomers, e.g. by special polymerization processes or by dissolution of the polymer in a solvent and spraying into a medium in which the solvent can evaporate or diffuse out of the particles. One such process is known, for example, from EP 466 986 B1. Suitable polymers are, for example, polycarbonates, polyurethanes, polyacrylates, polyolefins, polyesters or polyamides. Those spherical polymer powders whose primary particle diameter is less than 1 µm are particularly suitable. Those products based on a polymethacrylate copolymer are available commercially, for example, under the trade name Polytrap® Q5-6603 (Dow Corning). Other polymer powders, e.g. those based on polyamides (nylon 6, nylon 12), are available with a particle size of 2–10 µm (90%) and a specific surface area of ca. 10 m²/g under the trade name Orgasol® 2002 DU Nat Cos (Atochem S. A., Paris). Further spherical polymer powders which are suitable for the purpose according to the invention are, for example, the polymethacrylates (Micropearl M) from SEPPIC or (Plastic Powder A) from NIKKOL, the styrene-divinylbenzene copolymers (Platic Powder FP) from NIKKOL, the polyethylene and polypropylene powders (ACCUREL EP 400) from AKZO, and also silicone polymers (Silicone Powder X2–1605) from Dow Corning and also spherical cellulose powders.

The polymers are present in the agents used according to the invention preferably in amounts of 0.01 to 10% by weight, based on the overall agent. Amounts of from 0.1 to 5% by weight, in particular from 0.1 to 3% by weight, are particularly preferred.

In a further embodiment of the agents according to the invention, the effect can be further increased through the use of protein hydrolyzates and derivatives thereof. Protein hydrolyzates are product mixtures which are obtained by acidically, basically or enzymatically catalyzed degradation of proteins.

According to the invention, protein hydrolyzates used may either be of vegetable origin or of animal origin.

Animal protein hydrolyzates are, for example, elastin, collagen, keratin, silk and milk protein protein hydrolyzates, which may also be in the form of salts. Such products are sold, for example, under the trade names Dehylan® (Cognis), Promois® (Interorgana), Collapuron® (Cognis), Nutrilan® (Cognis), Gelita-Sol® (Deutsche Gelatine Fabriken Stoess & Co), Lexein® (Inolex) and Kerasol® (Croda).

According to the invention, preference is given to the use of protein hydrolyzates of vegetable origin, e.g. soybean, almond, rice, pea, potato and wheat protein hydrolyzates. Such products are obtainable, for example, under the trade names Gluadin® (Cognis), DiaMin® (Diamalt), Lexein® (Inolex) and Crotein® (Croda).

Although the use of protein hydrolyzates as such is preferred, it is possible to use instead of them amino acid mixtures which may have been obtained by another method, or individual amino acids such as, for example, arginine, lysine, histidine or pyrroglutamic acid. Likewise possible is the use of derivatives of protein hydrolyzates, for example in the form of their fatty acid condensation products. Such products are sold, for example, under the names Lamepon® (Cognis), Gluadin® (Cognis), Lexein® (Inolex), Crolastin (Croda) or Crotein® (Croda).

According to the invention, it is also possible to use cationized protein hydrolyzates, where the parent protein hydrolyzate can originate from animal, for example from collagen, milk or keratin, from plant, for example from wheat, corn, rice, potatoes, soybean or almonds, from marine life forms, for example from fish collagen or algae, or protein hydrolyzates obtained by biotechnological methods. The protein hydrolyzates forming the basis of the cationic derivatives according to the invention can be obtained from the corresponding proteins by a chemical, in particular alkaline or acidic, hydrolysis, by an enzymatic hydrolysis and/or a combination of the two types of hydrolysis. Hydrolysis of proteins usually gives a protein hydrolyzate with a molecular weight distribution of about 100 daltons up to several thousand daltons. Preference is given to those cationic protein hydrolyzates whose parent protein content has a molecular weight of from 100 up to 25 000 daltons, preferably 250 to 5000 daltons. In addition, cationic protein hydrolyzates are understood as meaning quaternized amino acids and mixtures thereof. Quaternization of the protein hydrolyzates or of the amino acids is often carried out using quaternary ammonium salts, such as, for example, N,N-dimethyl-N-(n-alkyl)-N-(2-hydroxy-3-chloro-n-propyl) ammonium halides. In addition, the cationic protein hydrolyzates can also be derivatized yet further. Typical examples of the cationic protein hydrolyzates and derivatives according to the invention which may be mentioned are the products given under the INCI names in the "International Cosmetic Ingredient Dictionary and Handbook", (seventh edition 1997, The Cosmetic, Toiletry and Fragrance Association 1101 17th Street, N.W., Suite 300, Washington, D.C. 20036-4702) and commercially available: Cocodimonium Hydroxypropyl Hydrolyzed Collagen, Cocodimonium Hydroxypropyl Hydrolyzed Casein, Cocodimonium Hydroxypropyl Hydrolyzed Collagen, Cocodimonium Hydroxypropyl Hydrolyzed Hair Keratin, Cocodimonium Hydroxypropyl Hydrolyzed Keratin, Cocodimonium Hydroxypropyl Hydrolyzed Rice Protein, Cocodimonium Hydroxypropyl Hydrolyzed Silk, Cocodimonium Hydroxypropyl Hydrolyzed Soy Protein, Cocodimonium Hydroxypropyl Hydrolyzed Wheat Protein, Cocodimonium Hydroxypropyl Silk Amino Acids, Hydroxypropyl Arginine Lauryl/Myristyl Ether HCl, Hydroxypropyltrimonium Gelatin, Hydroxypropyltrimonium Hydrolyzed Casein, Hydroxypropyltrimonium Hydrolyzed Collagen, Hydroxypropyltrimonium Hydrolyzed Conchiolin Protein, Hydroxypropyltrimonium Hydrolyzed keratin, Hydroxypropyltrimonium Hydrolyzed Rice Bran Protein, Hydroxypropyltrimonium Hydrolyzed Silk, Hydroxypropyltrimonium Hydrolyzed Soy Protein, Hydroxypropyl Hydrolyzed Vegetable Protein, Hydroxypropyltrimonium Hydrolyzed Wheat Protein, Hydroxypropyltrimonium Hydrolyzed Wheat Protein/Siloxysilicate, Laurdimonium Hydroxypropyl Hydrolyzed Soy Protein, Laurdimonium Hydroxypropyl Hydrolyzed Wheat Protein, Laurdimonium Hydroxypropyl Hydrolyzed Wheat Protein/Siloxysilicate, Lauryldimonium Hydroxypropyl Hydrolyzed Casein, Lauryldimonium Hydroxypropyl Hydrolyzed Collagen, Lauryldimonium Hydroxypropyl Hydrolyzed Keratin, Lauryldimonium Hydroxypropyl Hydrolyzed Silk, Lauryldimonium Hydroxypropyl Hydrolyzed Soy Protein, Steardimonium Hydroxypropyl Hydrolyzed Casein, Steardimonium Hydroxypropyl Hydrolyzed Collagen, Steardimonium Hydroxypropyl Hydrolyzed Keratin, Steardimonium Hydroxypropyl Hydrolyzed Rice Protein, Steardimonium Hydroxypropyl Hydrolyzed Silk, Steardimonium Hydroxypropyl Hydrolyzed Soy Protein, Steardimonium Hydroxypropyl Hydrolyzed Vegetable Protein, Steardimonium Hydroxypropyl Hydrolyzed Wheat Protein, Steartrimonium Hydroxyethyl Hydrolyzed Collagen, Quaternium-76 Hydrolyzed Collagen, Quaternium-79 Hydrolyzed Collagen, Quaternium-79 Hydrolyzed Keratin, Quaternium-79 Hydrolyzed Milk Protein, Quaternium-79 Hydrolyzed Silk, Quaternium-79 Hydrolyzed Soy Protein, Quaternium-79 Hydrolyzed Wheat Protein. Very particular preference is given to the vegetable-based cationic protein hydrolyzates and derivatives.

In the agents used according to the invention, the protein hydrolyzates and derivatives thereof are present in amounts of 0.01–10% by weight, based on the overall agent. Amounts of from 0.1 to 5% by weight, in particular 0.1 to 3% by weight, are very particularly preferred.

In a further preferred embodiment, the agents according to the invention comprise surfactants. The term surfactants is understood as meaning surface-active substances which carry an anionic or cationic charge in the molecule. It is also possible for both an anionic and also a cationic charge to be present in the molecule. These zwitterionic or amphoteric surface-active substances can likewise be used according to the invention. In addition, the surface-active substances may also be nonionic.

Suitable anionic surfactants in preparations according to the invention are all anionic surface-active substances suitable for use on the human body. These are characterized by a solubilizing anionic group, such as, for example, a carboxylate, sulfate, sulfonate or phosphate group, and a lipophilic alkyl group having about 8 to 30 carbon atoms. In addition, glycol or polyglycol ether groups, ester, ether and amide groups, and also hydroxyl groups may be present in the molecule. Examples of suitable anionic surfactants are, in each case in the form of the sodium, potassium and ammonium and also the mono-, di- and trialkanolammonium salts having 2 to 4 carbon atoms in the alkanol group, linear and branched fatty acids having 8 to 30 carbon atoms (soaps), ethercarboxylic acids of the formula R—O—(CH$_2$CH$_2$O)$_x$—CH$_2$—COOH in which R is a linear alkyl group having 8 to 30 carbon atoms and x=0 or 1 to 16, acyl sarcosides having 8 to 24 carbon atoms in the acyl group, acyl taurides having 8 to 24 carbon atoms in the acyl group, acyl isethionates having 8 to 24 carbon atoms in the acyl group, sulfosuccinic mono- and dialkyl esters having 8 to 24 carbon atoms in the alkyl group and sulfosuccinic monoalkyl polyoxyethyl esters having 8 to 24 carbon atoms in the alkyl group and 1 to 6 oxyethyl groups, linear alkanesufonates having 8 to 24 carbon atoms, linear alpha-olefinsulfonates having 8 to 24 carbon atoms, alpha-sulfofatty acid methyl esters of fatty acids having 8 to 30 carbon atoms, alkyl sulfates and alkyl polyglycol ether sulfates of the formula R—O(CH$_2$CH$_2$O)$_x$—OSO$_3$H in which R is a preferably linear alkyl group having 8 to 30 carbon atoms and x=0 or 1 to 12, mixtures of surface-active hydroxysulfonates according to DE-A-37 25 030, sulfated hydroxyalkyl polyethylene and/or hydroxyalkylene propylene glycol ethers according to DE-A-37 23 354, sulfonates of unsaturated fatty acids having 8 to 24 carbon atoms and 1 to 6 double bonds according to DE-A-39 26 344, esters of tartaric acid and citric acid with alcohols, which represent addition products of about 2–15 molecules of ethylene oxide and/or propylene oxide onto fatty alcohols having 8 to 22 carbon atoms, alkyl and/or alkenyl ether phosphates of the formula (VI)

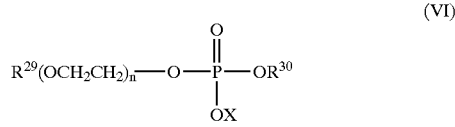

(VI)

in which R$^{29}$ is preferably an aliphatic hydrocarbon radical having 8 to 30 carbon atoms, R$^{30}$ is hydrogen, a radical .(CH$_2$CH$_2$O)$_n$R$^{29}$ or X, n is numbers from 1 to 10 and X is hydrogen, an alkali metal or alkaline earth metal or NR$^{31}$R$^{32}$R$^{33}$R$^{34}$, where R$^{31}$ to R$^{34}$, independently of one another, are a C$_1$ to C$_4$-hydrocarbon radical, sulfated fatty acid alkylene glycol esters of the formula (VII)

(VII)

in which R$^{35}$CO is a linear or branched, aliphatic, saturated and/or unsaturated acyl radical having 6 to 22 carbon atoms, Alk is CH$_2$CH$_2$, CHCH$_3$CH$_2$ and/or CH$_2$CHCH$_3$, n is numbers from 0.5 to 5 and M is a cation, as are described in DE-A 197 36 906.5, monoglyceride sulfates and monoglyceride ether sulfates of the formula (VIII):

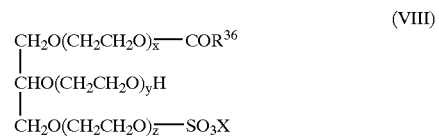

(VIII)

in which R$^{36}$CO is a linear or branched acyl radical having 6 to 22 carbon atoms, x, y and z are in total 0 or numbers from 1 to 30, preferably 2 to 10, and X is an alkali metal or alkaline earth metal. Typical examples of monoglyceride (ether) sulfates suitable for the purposes of the invention are the reaction products of lauric acid monoglyceride, coconut fatty acid monoglyceride, palmitic acid monoglyceride, stearic acid monoglyceride, oleic acid monoglyceride and tallow fatty acid monoglyceride, and also ethylene oxide adducts thereof with sulfur trioxide or chlorosulfonic acid in the form of its sodium salts. Preference is given to using monoglyceride sulfates of the formula (VIII) in which R$^{36}$CO is a linear acyl radical having 8 to 18 carbon atoms. Monoglyceride sulfates and monoglyceride ether sulfates are described, for example, in EP-B1 0 561 825, EP-B1 0 561 999, DE-A1 42 04 700 or by A. K. Biswas et al. in J. Am. Oil Chem. Soc. 37, 171 (1960) and F. U. Ahmed in J. Am. Oil Chem. Soc. 67, 8 (1990).

Preferred anionic surfactants are alkyl sulfates, alkylpolyglycol ether sulfates and ethercarboxylic acids having 10 to 18 carbon atoms in the alkyl group and up to 12 glycol ether groups in the molecule and sulfosuccinic mono and dialkyl esters having 8 to 18 carbon atoms in the alkyl group and sulfosuccinic monoalkyl polyoxyethyl esters having 8 to 18 carbon atoms in the alkyl group and 1 to 6 oxyethyl groups.

Zwitterionic surfactants is the term used to describe those surface-active compounds which carry at least one quaternary ammonium group and at least one —COO$^{(-)}$ or —SO$_3$$^{(-)}$ group in the molecule. Particularly suitable zwitterionic surfactants are the so-called betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl 3-hydroxyethylimidazolines having in each case 8 to 18 carbon atoms in the alkyl or acyl group, and cocoacylaminoethylhydroxyethyl carboxymethylglycinate. A preferred zwitterionic surfactant is the fatty acid amide derivative known under the INCI name Cocamidopropyl Betaine.

Ampholytic surfactants are understood as meaning those surface-active compounds which, apart from a C$_8$–C$_{24}$-alkyl or -acyl group in the molecule, contain at least one free amino group and at least one —COOH or —SO$_3$H group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 24 carbon atoms in the alkyl group. Particularly preferred ampholytic surfactants are N-cocoalkyl aminopropionate, cocoacyl aminoethylaminopropionate and C$_{12}$–C$_{18}$-acylsarcosine.

Nonionic surfactants contain, as hydrophilic group, e.g. a polyol group, a polyalkylene glycol ether group or a combination of polyol and polyglycol ether group. Such compounds are, for example, addition products of from 2 to 50 mol of ethylene oxide and/or 0 to 5 mol of propylene oxide onto linear and branched fatty alcohols having 8 to 30 carbon atoms, onto fatty acids having 8 to 30 carbon atoms and onto alkylphenols having 8 to 15 carbon atoms in the alkyl group, addition products, terminally capped with a methyl or $C_2$–$C_6$-alkyl radical, of from 2 to 50 mol of ethylene oxide and/or 0 to 5 mol of propylene oxide onto linear and branched fatty alcohols having 8 to 30 carbon atoms, onto fatty acids having 8 to 30 carbon atoms and onto alkylphenols having 8 to 15 carbon atoms in the alkyl group, such as, for example, the products obtainable under the trade names Dehydol® LS, Dehydol® LT (Cognis), $C_{12}$–$C_{30}$-fatty acid mono- and diesters of addition products of from 1 to 30 mol of ethylene oxide onto glycerol, addition products of from 5 to 60 mol of ethylene oxide onto castor oil and hydrogenated castor oil, polyol fatty acid esters, such as, for example, the commercial product Hydagen® HSP (Cognis) or Sovermol products (Cognis), alkoxylated triglycerides, alkoxylated fatty alkyl esters of the formula

$$R^{37}CO\text{—}(OCH_2CHR^{38})_wOR^{39}, \qquad (IX)$$

in which $R^{37}CO$ is a linear or branched, saturated and/or unsaturated acyl radical having 6 to 22 carbon atoms, $R^{38}$ is hydrogen or methyl, $R^{39}$ is linear or branched alkyl radicals having 1 to 4 carbon atoms and w is numbers from 1 to 20, amine oxides, hydroxy mixed ethers, as are described, for example, in DE-A 19738866, sorbitan fatty acid esters and addition products of ethylene oxide onto sorbitan fatty acid esters, such as, for example, the polysorbates, sugar fatty acid esters and addition products of ethylene oxide onto sugar fatty acid esters, addition products of ethylene oxide onto fatty acid alkanolamides and fatty amines, fatty acid N-alkylglucamides, alkyl polyglycosides corresponding to the general formula RO—$(Z)_x$, where R is alkyl, Z is sugar, and x is the number of sugar units. The alkyl polyglycosides which can be used according to the invention can contain just a certain alkyl radical R. Usually, however, these compounds are prepared starting from natural fats and oils or mineral oils. In this case, the alkyl radicals R are mixtures corresponding to the starting compounds or corresponding to the respective work-up of these compounds.

Particular preference is given to those alkyl polyglycosides in which R consists essentially of $C_8$- and $C_{10}$-alkyl groups,
essentially of $C_{12}$- and $C_{14}$-alkyl groups,
essentially of $C_8$- to $C_{16}$-alkyl groups or
essentially of $C_{12}$- to $C_{16}$-alkyl groups or
essentially of $C_{16}$- to $C_{18}$-alkyl groups.

As sugar building block Z, it is possible to use any mono- or oligosaccharides. Usually, sugars having 5 or 6 carbon atoms, and the corresponding oligosaccharides are used. Such sugars are, for example, glucose, fructose, galactose, arabinose, ribose, xylose, lyxose, allose, altrose, mannose, gulose, idose, talose and sucrose. Preferred sugar building blocks are glucose, fructose, galactose, arabinose and sucrose; glucose is particularly preferred.

The alkyl polyglycosides which can be used according to the invention contain, on average, 1.1 to 5 sugar units. Alkyl polyglycosides with x values of from 1.1 to 2.0 are preferred. Very particular preference is given to alkyl glycosides in which x is 1.1 to 1.8.

The alkoxylated homologs of said alkyl polyglycosides can also be used according to the invention. These homologs can, on average, contain up to 10 ethylene oxide and/or propylene oxide units per alkyl glycoside unit.

Preferred nonionic surfactants have proven to be the alkylene oxide addition products onto saturated linear fatty alcohols and fatty acids having in each case 2 to 30 mol of ethylene oxide per mole of fatty alcohol or fatty acid. Preparations with excellent properties are likewise obtained if they comprise, as nonionic surfactants, fatty acid esters of ethoxylated glycerol.

These compounds are characterized by the following parameters. The alkyl radical R contains 6 to 22 carbon atoms and may either be linear or branched. Preference is given to primary linear aliphatic radicals and aliphatic radicals methyl-branched in the 2-position. Such alkyl radicals are, for example, 1-octyl, 1-decyl, 1-lauryl, 1-myristyl, 1-cetyl and 1-stearyl. Particular preference is given to 1-octyl, 1-decyl, 1-lauryl, 1-myristyl. If so-called "oxo alcohols" are used as starting materials, compounds with an odd number of carbon atoms in the alkyl chain predominate.

The compounds containing alkyl groups used as surfactant may in each case be uniform substances. It is, however, usually preferred to start, in the preparation of these substances, from native vegetable or animal raw materials, thus giving mixtures of substances with different alkyl chain lengths dependent on the raw material in question.

For the surfactants which represent addition products of ethylene oxide and/or propylene oxide onto fatty alcohols or derivatives of these addition products, it is possible to use either products with a "normal" homolog distribution, or those with a narrowed homolog distribution. "Normal" homolog distribution is understood as meaning here mixtures of homologs which are obtained in the reaction of fatty alcohol and alkylene oxide using alkali metals, alkali metal hydroxides and alkali metal alkoxides as catalysts. Narrowed homolog distributions are obtained, by contrast, when, for example, hydrotalcites, alkaline earth metal salts of ethercarboxylic acids, alkaline earth metal oxides, hydroxides or alkoxides are used as catalysts. The use of products with narrowed homolog distribution may be preferred.

These surfactants are used in amounts of 0.1–45% by weight, preferably 1–30% by weight and very particularly preferably 1–15% by weight, based on the overall agent.

In a preferred embodiment, nonionic, zwitterionic and/or amphoteric surfactants, and mixtures thereof, may be preferred.

According to the invention, it is likewise possible to use cationic surfactants of the quaternary ammonium compound type, the ester quat type and the amidoamine type. Preferred quaternary ammonium compounds are ammonium halides, in particular chlorides and bromides, such as alkyltrimethylammonium chlorides, dialkyldimethylammonium chlorides and trialkylmethylammonium chlorides, e.g. cetyltrimethylammonium chloride, stearyltrimethylammonium chloride, distearyldimethyl-ammonium chloride, lauryldimethylammonium chloride, lauryldimethylbenzylammonium chloride and tricetylmethylammonium chloride, and the imidazolium compounds known under the INCI names Quaternium-27 and Quaternium-83. The long alkyl chains of the abovementioned surfactants preferably have 10 to 18 carbon atoms.

Ester quats are known substances which contain either at least one ester function or at least one quaternary ammonium group as structural element. Preferred ester quats are quaternized ester salts of fatty acids with triethanolamine, quaternized ester salts of fatty acids with diethanolalkylamines and quaternized ester salts of fatty acids with 1,2-dihydroxypropyldialkylamines. Such products are sold, for example, under the trade names Stepantex®, Dehyquart® and Armocare®. The products Armocare® VGH-70, an N,N-bis(2-palmitoyloxyethyl)dimethylammonium chloride, and also Dehyquart® F-75, Dehyquart® C-4046, Dehyquart® L80 and Dehyquart® AU-35 are examples of such ester quats.

The alkylamidoamines are usually prepared by amidation of natural or synthetic fatty acids and fatty acid cuts with dialkylaminoamines. A particularly suitable compound from this group of substances according to the invention is stearamidopropyldimethylamine available commercially under the name Tegoamid® S 18.

The cationic surfactants are present in the agents used according to the invention preferably in amounts of from 0.05 to 10% by weight, based on the overall agent. Amounts of from 0.1 to 5% by weight are particularly preferred.

In a further preferred embodiment, the action of the active ingredient according to the invention can be increased by emulsifiers. Such emulsifiers are, for example:

addition products of from 4 to 30 mol of ethylene oxide and/or 0 to 5 mol of propylene oxide onto linear fatty alcohols having 8 to 22 carbon atoms, onto fatty acids having 12 to 22 carbon atoms and onto alkylphenols having 8 to 15 carbon atoms in the alkyl group, $C_{12}$–$C_{22}$-fatty acid mono- and diesters of addition products of from 1 to 30 mol of ethylene oxide onto polyols having 3 to 6 carbon atoms, in particular onto glycerol, ethylene oxide and polyglycerol addition products onto methyl glucoside fatty acid esters, fatty acid alkanolamides and fatty acid glucamides, $C_8$–$C_{22}$-alkyl mono- and oligoglycosides and ethoxylated analogs thereof, where degrees of oligomerization of from 1.1 to 5, in particular 1.2 to 2.0, and glucose as sugar component are preferred, mixtures of alkyl (oligo)glucosides and fatty alcohols, for example the commercially available product Montanov® 68, addition products of from 5 to 60 mol of ethylene oxide onto castor oil and hydrogenated castor oil, partial esters of polyols having 3–6 carbon atoms with saturated fatty acids having 8 to 22 carbon atoms, sterols. Sterols are understood as meaning a group of steroids which carry a hydroxyl group on the 3rd carbon atom of the steroid backbone and are isolated both from animal tissue (zoosterols) and from vegetable fats (phytosterols). Examples of zoosterols are cholesterol and lanosterol. Examples of suitable phytosterols are ergosterol, stigmasterol and sitosterol. Sterols are also isolated from fungi and yeasts, these being termed micosterols.

Phospholipids. These are understood as meaning primarily the glucose phospholipids which are obtained, for example, as lecithins or phosphatidylcholines from, for example, egg yolk or plant seeds (e.g. soybeans).

Fatty acid esters of sugars and sugar alcohols, such as sorbitol, polyglycerols and polyglycerol derivatives, such as, for example, polyglycerol poly-12-hydroxystearate (commercial product Dehymuls® PGPH), linear and branched fatty acids having 8 to 30 carbon atoms and their Na, K, ammonium, Ca, Mg and Zn salts.

The agents according to the invention comprise the emulsifiers preferably in amounts of 0.1–25% by weight, in particular 0.5–15% by weight, based on the overall agent.

Preferably, the compositions according to the invention can comprise at least one nonionic emulsifier with an HLB value of from 8 to 18, according to the definitions given in Römpp Lexikon Chemie (Ed. J. Falbe, M. Regitz), 10th edition, Georg Thieme Verlag Stuttgart, New York, (1997), page 1764. Nonionogenic emulsifiers with an HLB value of 10–15 may be particularly preferred according to the invention.

Among said emulsifier types, the emulsifiers which do not contain ethylene oxide and/or propylene oxide in the molecule may be very particularly preferred.

In a further preferred embodiment of the invention, the effect of the active ingredient according to the invention can be further optimized by fatty substances. Fatty substances are understood as meaning fatty acids, fatty alcohols, natural and synthetic waxes, which may either be in solid form or else in liquid form in aqueous dispersion, and natural and synthetic cosmetic oil components.

Fatty acids which can be used are linear and/or branched, saturated and/or unsaturated fatty acids having 6–30 carbon atoms. Preference is given to fatty acids having 10–22 carbon atoms. Examples thereof which can be mentioned are the isostearic acids, such as the commercial products Emersol® 871 and Emersol® 875, and isopalmitic acids, such as the commercial product Edenor® IP 95, and all other fatty acids sold under the trade names Edenor® (Cognis). Further typical examples of such fatty acids are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachidic acid, gadoleic acid, behenic acid and erucic acid, and technical-grade mixtures thereof which are produced, for example, during the pressurized cleavage of natural fats and oils, in the oxidation of aldehydes from the Roelen oxo synthesis or the dimerization of unsaturated fatty acids. Particular preference is usually given to the fatty acid cuts which are obtainable from coconut oil and palm oil; particular preference is usually given to the use of stearic acid.

The use amount here is 0.1–15% by weight, based on the overall agent. In a preferred embodiment, the amount is 0.5–10% by weight, amounts of 1–5% by weight being very particularly advantageous. Fatty alcohols which can be used are saturated, mono- or polyunsaturated, branched or unbranched fatty alcohols having $C_6$–$C_{30}$-, preferably $C_{10}$–$C_{22}$- and very particularly preferably $C_{12}$–$C_{22}$-carbon atoms. For the purposes of the invention, it is possible, for example, to use decanol, octanol, octenol, dodecenol, decenol, octadienol, dodecadienol, decadienol, oleyl alcohol, erucyl alcohol, ricinol alcohol, stearyl alcohol, isostearyl alcohol, cetyl alcohol, lauryl alcohol, myristyl alcohol, arachidyl alcohol, capryl alcohol, capric alcohol, linoleyl alcohol, linolenyl alcohol and behenyl alcohol, and Guerbet alcohols thereof, the intention being for the character of this list to be exemplary and nonlimiting. However, the fatty alcohols originate from preferably natural fatty acids, in which case it is usually possible to start from an isolation of the esters of the fatty acids by reduction. According to the invention, it is likewise possible to use those fatty alcohol cuts which are produced by reducing naturally occurring triglycerides such as beef tallow, palm oil, peanut oil, rape oil, cottonseed oil, soybean oil, sunflower oil and linseed oil or fatty acid esters arising from their transesterification products with corresponding alcohols, and thus represent a mixture of different fatty alcohols. Such substances are available commercially, for example, under the names Stenol®, e.g. Stenol® 1618 or Lanette®, e.g. Lanette® O or Lorol®, e.g. Lorol® C8, Lorol® C14, Lorol® C18, Lorol® C8–18, HD-Ocenol®, Crodacol®, e.g. Crodacol® CS, Novol®, Eutanol® G, Guerbitol® 16, Guerbitol® 18, Guerbitol® 20, Isofol® 12, Isofol® 16, Isofol® 24, Isofol® 36, Isocarb® 12, Isocarb® 16 or Isocarb® 24. According to the invention, it is also of course possible to use wool wax alcohols, as are available commercially, for example, under the names Corona®, White Swan®, Coronet® or Fluilan®. The fatty alcohols are used in amounts of 0.1–20% by weight, based on the total preparation, preferably in amounts of 0.1–10% by weight.

Natural or synthetic waxes which can be used according to the invention are solid paraffins or isoparaffins, carnauba waxes, beeswaxes, candelilla waxes, ozokerite, ceresine, spermaceti wax, sunflower wax, fruit waxes, such as, for example, apple wax or citrus wax, microcrystalline waxes of PE or PP. Such waxes are available, for example, from Kahl & Co., Trittau.

The natural and synthetic cosmetic oily bodies which can increase the effect of the active ingredient according to the invention include, for example:

vegetable oils. Examples of such oils are sunflower oil, olive oil, soybean oil, rapeseed oil, almond oil, jojoba oil, orange oil, wheatgerm oil, peach kernel oil and the liquid fractions of coconut oil. Also suitable, however, are other triglyceride oils, such as the liquid fractions of beef tallow and synthetic triglyceride oils.

Liquid paraffin oils, isoparaffin oils and synthetic hydrocarbons, and di-n-alkyl ethers having a total of between 12 and 36 carbon atoms, in particular 12 to 24 carbon atoms, such as, for example, di-n-octyl ether, di-n-decyl ether, di-n-nonyl ether, di-n-undecyl ether, di-n-dodecyl ether, n-hexyl n-octyl ether, n-octyl n-decyl ether, n-decyl n-undecyl ether, n-undecyl n-dodecyl ether and n-hexyl n-undecyl ether and di-tert-butyl ether, diisopentyl ether, di-3-ethyl decyl ether, tert-butyl n-octyl ether, isopentyl n-octyl ether and 2-methylpentyl n-octyl ether. The compounds 1,3-di(2-ethylhexyl)cyclohexane (Cetiol® S) and di-n-octyl ether (Cetiol® OE), available as commercial products, may be preferred.

Ester oils. Ester oils are understood as meaning the esters of $C_6$–$C_{30}$-fatty acids with $C_2$–$C_{30}$-fatty alcohols. Preference is given to the monoesters of fatty acids with alcohols having 2 to 24 carbon atoms. Examples of fatty acid components used in the esters are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachidic acid, gadoleic acid, behenic acid and erucic acid, and technical-grade mixtures thereof, which are produced, for example, during the pressurized cleavage of natural fats and oils, during the oxidation of aldehydes from the Roelen oxo synthesis or the dimerization of unsaturated fatty acids. Examples of the fatty alcohol components in the ester oils are isoproyl alcohol, caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol, and technical-grade mixtures thereof which are produced, for example, during the high-pressure hydrogenation of technical-grade methyl esters based on fats and oils or aldehydes from the Roelen oxo synthesis, and as monomer fraction in the dimerization of unsaturated fatty alcohols. According to the invention, particular preference is given to isopropyl myristate (Rilanit® IPM), isononanoic acid $C_{16}$–$C_{18}$-alkyl esters (Cetiol® SN), 2-ethylhexyl palmitate (Cegesoft® 24), 2-ethylhexyl stearate (Cetiol® 868), cetyl oleate, glycerol tricaprylate, coconut fatty alcohol caprate/caprylate (Cetiol® LC), n-butyl stearate, oleyl erucate (Cetiol® J 600), isopropyl palmitate (Rilanit® IPP), oleyl oleate (Cetiol®), hexyl laurate (Cetiol® A), di-n-butyl adipate (Cetiol® B), myristyl myristate (Cetiol® MM), cetearyl isononanoate (Cetiol® SN), decyl oleate (Cetiol® V).

Dicarboxylic esters, such as di-n-butyl adipate, di(2-ethylhexyl) adipate, di(2-ethylhexyl) succinate and diisotridecyl acelate, and diol esters, such as ethylene glycol dioleate, ethylene glycol diisotridecanoate, propylene glycol di(2-ethylhexanoate), propylene glycol diisostearate, propylene glycol diperlargonate, butanediol diisostearate, neopentyl glycol dicaprylate, symmetrical, asymmetrical or cyclic esters of carbonic acid with fatty alcohols, for example described in DE-A 197 56 454, glycerol carbonate or dicaprylyl carbonate (Cetiol® CC), mono-, di- and trifatty acid esters of saturated and/or unsaturated linear and/or branched fatty acids with glycerol, such as, for example, Monomuls® 90–018, Monomuls® 90-L12 or Cutina® MD.

The use amount is 0.1–50% by weight, based on the overall agent, preferably 0.1–20% by weight and particularly preferably 0.1–15% by weight, based on the total agent.

The total amount of oil and fatty components in the agents according to the invention is usually 6–45% by weight, based on the overall agent. Amounts of 10–35% by weight are preferred according to the invention.

In addition, it has been found that the effect of the active ingredient according to the invention can be increased if it is combined with hydroxycarboxylic esters. Preferred hydroxycarboxylic esters are complete esters of glycolic acid, lactic acid, malic acid, tartaric acid or citric acid. Further hydroxycarboxylic esters which are suitable in principle are esters of β-hydroxypropionic acid, of tartronic acid, of D-gluconic acid, sugar acid, mucic acid or glucuronic acid. Suitable as alcohol component of these esters are primary, linear or branched aliphatic alcohols having 8–22 carbon atoms, e.g. fatty alcohols or synthetic fatty alcohols. In this connection, particular preference is given to the esters of $C_{12}$–$C_{15}$-fatty alcohols. Esters of this type are available commercially, e.g. under the trade name Cosmacol® from EniChem, Augusta Industriale. The use amount of the hydroxycarboxylic esters here is 0.1–15% by weight, based on the agent, preferably 0.1–10% by weight and very particularly preferably 0.1–5% by weight.

Likewise, the combination of the active ingredient with vitamins, provitamins and vitamin precursors and derivatives thereof has proven advantageous.

In this connection, according to the invention, preference is given to those vitamins, provitamins and vitamin precursors which are usually assigned to the groups A, B, C, E, F and H.

The group of substances referred to as vitamin A includes retinol (vitamin $A_1$) and 3,4-didehydroretinol (vitamin $A_2$). β-carotene is the provitamin of retinol. Suitable as vitamin A component are, according to the invention, for example vitamin A acid and esters thereof, vitamin A aldehyde and vitamin A alcohol, and esters thereof, such as the palmitate and the acetate. The preparations used according to the invention comprise the vitamin A component preferably in amounts of 0.05–1% by weight, based on the overall preparation.

The vitamin B group or the vitamin B complex include, inter alia, vitamin $B_1$ (thiamine)

vitamin $B_2$ (riboflavin)

vitamin $B_3$. Under this term are often listed the compounds nicotinic acid and nicotinamide (niacinamide). According to the invention, preference is given to nicotinamide, which is present in the agents used according to the invention preferably in amounts of from 0.05 to 1% by weight, based on the overall agent.

Vitamin $B_5$ (pantothenic acid and panthenol). Within this group, preference is given to using panthenol. Derivatives of panthenol which can be used according to the invention are, in particular, the esters and ethers of panthenol, and also cationically derivatized panthenols. Individual representatives are, for example, panthenol triacetate, panthenol monoethyl ether and its monoacetate, and the cationic panthenol derivatives disclosed in WO 92/13829. Said compounds of the vitamin $B_5$ type are present in the agents used according to the invention preferably in amounts of 0.05–10% by weight, based on the overall agent. Amounts of 0.1–5% by weight are particularly preferred.

Vitamin $B_6$ (pyridoxine and pyridoxamine and pyridoxal).

Vitamin C (ascorbic acid). Vitamin C is used in the agents used according to the invention preferably in amounts of from 0.1 to 3% by weight, based on the overall agent. The use in the form of the palmitic ester, the glucosides or phosphates may be preferred. The use in combination with tocopherols may likewise be preferred.

Vitamin E (tocopherols, in particular α-tocopherol) Tocopherol and its derivatives, which covers, in particular, the esters, such as the acetate, the nicotinate, the phosphate and the succinate, are present in the agents used according to the invention preferably in amounts of 0.05–1% by weight, based on the overall agent.

Vitamin F. The term "vitamin F" is usually understood as meaning essential fatty acids, in particular linoleic acid, linolenic acid and arachidonic acid.

Vitamin H. Vitamin H is used to refer to the compound (3aS,4S,6aR)-2-oxohexahydrothienol[3,4-d]imidazole-4-valeric acid, which has in the meantime become known by the trivial name biotin. Biotin is present in the agents used according to the invention preferably in amounts of from 0.0001 to 1.0% by weight, in particular in amounts of from 0.001 to 0.01% by weight.

The agents used according to the invention preferably comprise vitamins, provitamins and vitamin precursors from the groups A, B, E and H.

Panthenol and its derivatives and also nicotinamide and biotin are particularly preferred.

Finally, the action of the active ingredient can also be increased through the combined use of plant extracts.

Usually, these extracts are prepared by extraction of the whole plant. However, it may also be preferred in individual cases to prepare the extracts exclusively from flowers and/or leaves of the plant.

With regard to the plant extracts which can be used according to the invention, reference is made in particular to the extracts which are listed in the table starting on page 44 of the 3rd edition of the introduction to the ingredient declaration of cosmetic products, published by the Industrieverband Körperpflege- und Waschmittel e.V. (IKW), Frankfurt.

According to the invention, the extracts from green tea, oak bark, stinging nettle, hamamelis, hops, chamomile, burdock, horsetail, whitethorn, linden blossom, almond, aloe vera, spruce needle, horse chestnut, sandalwood, juniper, coconut, mango, apricot, lemon, wheat, kiwi, melon, orange, grapefruit, sage, rosemary, birch, mallow, lady's-smock, wild thyme, yarrow, thyme, melissa, restharrow, coltsfoot, marshmallow, meristem, ginseng and root ginger, in particular, are preferred.

Particular preference is given to the extracts from green tea, oak bark, stinging nettle, hamamelis, hops, chamomile, burdock, horsetail, linden blossom, almond, aloe vera, coconut, mango, apricot, lemon, wheat, kiwi, melon, orange, grapefruit, sage, rosemary, birch, lady's-smock, wild thyme, yarrow, restharrow, meristem, ginseng and root ginger.

Very particularly suitable for the use according to the invention are the extracts from green tea, almond, aloe vera, coconut, mango, apricot, lemon, wheat, kiwi and melon.

The extractants used for the preparation of said plant extracts may be water, alcohols and mixtures thereof. Of the alcohols, preference is given in this connection to lower alcohols, such as ethanol and isopropanol, but in particular polyhydric alcohols, such as ethylene glycol and propylene glycol, both as a sole extractant and also in a mixture with water. Plant extracts based on water/propylene glycol in the ratio 1:10 to 10:1 have proven particularly suitable.

According to the invention, the plant extracts can be used both in pure form and also in dilute form. If they are used in dilute form, they usually comprise about 2–80% by weight of active substance and, as solvent, the extractant or extractant mixture used in their isolation.

In addition, it may be preferred to use mixtures of two or more, in particular two, different plant extracts in the agents according to the invention.

In addition, it has been found that the effect of the active ingredient according to the invention in cosmetic agents can be further increased in combination with substances which contain primary or secondary amino groups. Examples of such amino compounds which may be mentioned are ammonia, monoethanolamine, 2-amino-2-methyl-1-propanol, 2-amino-2-methylpropanediol, and basic amino acids, such as, for example, lysine, arginine or histidine. These amines can of course also be used in the form of the corresponding salts with inorganic and/or organic acids, such as, for example, in the form of ammonium carbonate, ammonium citrate, ammonium oxalate, ammonium tartrate or lysine hydrochloride. The amines are used together with the active ingredient according to the invention in ratios of from 1:10 to 10:1, preferably 3:1 to 1:3 and very particularly preferably in stoichiometric amounts.

In addition to the active ingredient which is obligatorily required according to the invention and the further, above mentioned preferred components, these preparations can in principle comprise all further components known to the person skilled in the art for such cosmetic agents.

Further active ingredients, auxiliaries and additives are, for example:

- thickeners, such as gelatin or plant gums, for example agar agar, guar gum, alginates, xanthan gum, gum arabic, karaya gum, carob seed grain, linseed gums, dextrans, cellulose derivatives, e.g. methylcellulose, hydroxyalkylcellulose and carboxymethylcellulose, starch fractions and derivatives, such as amylose, amylopectin and dextrins, clays and phyllosilicates, such as, for example, bentonite or completely synthetic hydrocolloids, such as, for example, polyvinyl alcohol, the Ca, Mg or Zn soaps,
- structurants, such as maleic acid and lactic acid,
- perfume oils,
- dimethyl isosorbide,
- cyclodextrins,
- solvents and solubility promoters, such as ethanol, isopropanol, ethylene glycol, propylene glycol, glycerol and diethylene glycol,
- fiber structure-improving active ingredients, in particular mono-, di- and oligosaccharides, such as, for example, glucose, galactose, fructose, fruit sugar and lactose,
- quaternized amines, such as methyl-1-alkylamidoethyl-2-alkylimidazolinium methosulfate,
- defoamers, such as silicones,
- dyes for coloring the agent,
- antidandruff active ingredients, such as piroctone olamine, zinc omadine and climbazole,
- light protection agents, in particular derivatized benzophenones, cinnamic acid derivatives and triazines,
- further substances for adjusting the pH, such as, for example, α- and β-hydroxycarboxylic acids,
- active ingredients, such as allantoin and bisabolol,
- cholesterol,
- complexing agents, such as EDTA, NTA, β-alaninediacetic acid and phosphonic acids,
- swelling and penetration substances, such as glycerol, propylene glycol monoethyl ether, carbonates, hydrogencarbonates, guanidines, ureas and primary, secondary and tertiary phosphates,
- ceramides. Ceramides are understood as meaning N-acylsphingosine (fatty acid amides of sphingosine) or synthetic analogs of such lipids (so-called pseudoceramides),
- opacifiers, such as latex, styrene/PVP and styrene/acrylamide copolymers,
- pearlizers, such as ethylene glycol mono- and distearate and also PEG-3 distearate,
- pigments,
- reducing agents, such as, for example, thioglycolic acid and derivatives thereof, thiolactic acid, cysteamine, thiomalic acid and α-mercaptoethanesulfonic acid,
- propellants, such as propane-butane mixtures, $N_2O$, dimethyl ether, $CO_2$ and air,
- antioxidants,
- deoxy sugars,
- plant glycosides,
- polysaccharides, such as fucose or rhamnose.

With regard to further optional components and the amount of these components used, reference is made expressly to the relevant handbooks known to those skilled in the art, e.g. the monograph by Kh. Schrader, Grundlagen und Rezepturen der Kosmetika [Principles and formulations of cosmetics], 2nd edition, Hüthig Buch Verlag, Heidelberg, 1989.

With regard to the nature according to which the active ingredient according to the invention is applied to the keratin fibers, in particular human hair, and also to the skin, there are in principle no limitations. Suitable formulation forms of these preparations are, for example, creams, lotions, solutions, tonics, emulsions, such as W/O, O/W, PIT emulsions (emulsions in accordance with the teaching of phase inversion, called PIT), microemulsions and multiple emulsions, coarse, unstable, single- or multiphase shaking mixtures, gels, sprays, aerosols and foam aerosols. These are usually formulated on an aqueous or aqueous-alcoholic basis. Alcoholic components which may be used here are lower alkanols and also polyols, such as propylene glycol and glycerol. Ethanol and isopropanol are preferred alcohols. Water and alcohol may be present in the aqueous-alcoholic base in a weight ratio of from 1:10 to 10:1. Water and aqueous-alcoholic mixtures which comprise up to 50% by weight, in particular up to 25% by weight, of alcohol, based on the mixture of alcohol/water, may be preferred bases in accordance with the invention. The pH of these preparations may in principle be from 2–11. It is preferably between 2 and 7, values from 3 to 5 being particularly preferred. To set the pH, virtually any acid or base which can he used for cosmetic purposes can be used. Usually, the acids used are food acids. Food acids are understood as meaning those acids which are consumed in the course of usual eating and have positive effects on the human organism. Food acids are, for example, acetic acid, lactic acid, tartaric acid, citric acid, malic acid, ascorbic acid and gluconic acid. For the purposes of the invention, the use of citric acid and lactic acid is particularly preferred. Preferred bases are ammonia, alkali metal hydroxides, monoethanolamine, triethanolamine and N,N,N',N'-tetrakis(2-hydroxypropyl)ethylenediamine.

Preparations which remain on the skin and the hair have proven particularly effective and can therefore represent preferred embodiments of the teaching according to the invention. "Remaining on the skin and the hair" is understood according to the invention as meaning those preparations which, in the course of treatment, are not rinsed off the skin or rinsed out of the hair again after a period of from a few seconds to one hour using water or an aqueous solution. Rather, the preparations remain on the skin or the hair until the next wash.

According to a preferred embodiment for application to the hair, these preparations are formulated as hair treatment or hair conditioner. The preparations of the invention according to this embodiment can, following expiry of this contact time, be rinsed out with water or an at least predominantly water-containing agent; however, as stated above, they are preferably left on the hair. In this connection, it may be preferred to apply the preparation according to the invention to the hair prior to the application of a cleaning agent, a waving agent or other hair-treatment agents. In this case, the preparation according to the invention serves as color protection for the subsequent applications.

According to further embodiments, the agents according to the invention may, however, also, for example, be cleaning agents for skin and hair, such as shampoos, make-up removers, face cleansers, care agents for skin and hair, such as rinses, day creams, night creams, face masks, or setting agents for the hair, such as hair-setting agents, setting foams, styling gels and low-waving agents, permanent shaping agents, such as permanent-waving and neutralization agents and pretreatment agents or afterrinses used in particular in the course of a permanent-waving process or coloring process.

In a particular embodiment of the agents according to the invention, it may be preferred for the agents to be in the form of a microemulsion. For the purposes of the invention, microemulsions are likewise understood as meaning so-called "PIT" emulsions. These emulsions are in principle systems with the 3 components water, oil and emulsifier which, at room temperature, are in the form of an oil-in-water (O/W) emulsion. As these systems are heated, microemulsions form in a certain temperature range (usually referred to as the phase inversion temperature or "PIT"), which, upon further heating, convert to water-in-oil (W/O) emulsions. Upon subsequent cooling, O/W emulsions are again formed, although, even at room temperature, they are in the form of microemulsions with an average particle diameter of less than 400 nm, in particular with a particle diameter of about 100–300 nm. Details regarding these very stable, low-viscosity systems, for which the term "PIT emulsions" has generally been adopted, are given in a large number of publications, for which the publications in Angew. Chem. 97, 655–669 (1985) and Adv. Colloid Interface Sci 58, 119–149 (1995) are mentioned by way of representation.

According to the invention, preference may be given to those micro- or "PIT" emulsions which have an average particle diameter of about 200 nm.

The microemulsions according to the invention can be prepared, for example, by firstly determining the phase inversion temperature of the system by heating a sample of the emulsion prepared in the customary manner and, using a conductivity measuring instrument, determining the temperature at which the conductivity decreases greatly. The decrease in the specific conductivity of the O/W emulsion initially present generally decreases over a temperature range from 2 to 8° C. from originally more than 1 mS/cm to values below 0.1 mS/cm. This temperature range corresponds then to the phase inversion temperature range. After the phase inversion temperature range is thus known, the emulsion, initially prepared as is customary, comprising oil component, nonionogenic emulsifier, at least parts of water and optionally further components can be heated to a temperature which is within or above the phase inversion temperature range, then cooled, and, where appropriate, further components and the remaining water can be added. Alternatively, the microemulsion can also be prepared directly at a temperature which is within or above the phase inversion temperature range. The microemulsion prepared in this way is then cooled to a temperature below the phase inversion temperature range, usually room temperature.

In a very particularly preferred embodiment, the active ingredient is used in agents for coloring keratin fibers. In this connection, the active ingredient according to the invention can in principle be added directly to the colorant. Preferably, the active ingredient is applied to the colored keratin fiber, but in a separate step, either directly after the actual dyeing process, or in separate treatments, where appropriate even days or weeks after the dyeing process.

The term dyeing process includes here all processes known to the person skilled in the art in which a colorant is applied to the, optionally dampened, hair, and the colorant is either left on the hair for a period between a few minutes and about 45 minutes and then rinsed out with water or a surfactant-containing agent, or is entirely left on the hair. In this connection, reference is made expressly to the known monographs, e.g. Kh. Schrader, Grundlagen und Rezepturen der Kosmetika [Principles and formulations of cosmetics], 2nd edition, Hüthig Buch Verlag, Heidelberg, 1989, which state the relevant knowledge of the person skilled in the art.

As already mentioned above, within the scope of the teaching according to the invention, it is also possible, although less preferable, to incorporate the active ingredient directly into the colorant or tint.

The composition of the colorant or tint is not subject to any limitations in principle.

As dye (precursor), it is possible to use
 oxidation dye precursors of the developer and coupler type,
 natural and synthetic direct dyes and
 precursors of nature-analogous dyes, such as indole and indoline derivatives, and
mixtures of representatives of one or more of these groups.

The oxidation dye precursors of the developer type customarily used are primary aromatic amines with a further free or substituted hydroxyl or amino group situated in the para or ortho position, diaminopyridine derivatives, heterocyclic hydrazones, 4-aminopyrazole derivatives, and 2,4,5,6-tetraaminopyrimidine and derivatives thereof. Suitable developer components are, for example, p-phenylenediamine, p-tolylenediamine, p-aminophenol, o-aminophenol, 1-(2'-hydroxyethyl)-2,5-diaminobenzene, N,N-bis(2-hydroxyethyl)-p-phenylenediamine, 2-(2,5-diaminophenoxy)ethanol, 4-amino-3-methylphenol, 2,4,5,6-tetraaminopyrimidine, 2-hydroxy-4,5,6-triaminopyrimidine, 4-hydroxy-2,5,6-triaminopyrimidine, 2,4-dihydroxy-5,6-diaminopyrimidine, 2-di-methylamino-4,5,6-triaminopyrimidine, 2-hydroxymethylamino-4-aminophenol, bis(4-aminophenyl)amine, 4-amino-3-fluorophenol, 2-aminomethyl-4-aminophenol, 2-hydroxymethyl-4-aminophenol, 4-amino-2-((diethylamino)methyl)phenol, bis(2-hydroxy-5-aminophenyl)methane, 1,4-bis(4-aminophenyl)diazacycloheptane, 1,3-bis(N(2-hydroxyethyl)-N(4-aminophenylamino))-2-propanol, 4-amino-2-(2-hydroxyethoxy)phenol, 1,10-bis(2,5-diaminophenyl)-1,4,7,10-tetraoxadecane, and 4,5-diaminopyrazole derivatives as claimed in EP 0 740 741 and WO 94/08970, such as, for example, 4,5-diamino-1-(2'-hydroxyethyl)pyrazole. Particularly advantageous developer components are p-phenylenediamine, p-tolylenediamine, p-aminophenol, 1-(2'-hydroxyethyl)-2,5-diaminobenzene, 4-amino-3-methylphenol, 2-aminomethyl-4-aminophenol, 2,4,5,6-tetraaminopyrimidine, 2-hydroxy-4,5,6-triaminopyrimidine, 4-hydroxy-2,5,6-triaminopyrimidine.

Oxidation dye precursors of the coupler type which are used are usually m-phenylenediamine derivatives, naphthols, resorcinol and resorcinol derivatives, pyrazolones and m-aminophenol derivatives. Examples of such coupler components are
 m-aminophenol and derivatives thereof such as, for example, 5-amino-2-methylphenol, 5-(3-hydroxypropylamino)-2-methylphenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-(diethylamino)phenol, N-cyclopentyl-3-aminophenol, 1,3-dihydroxy-5-

(methylamino)benzene, 3-(ethylamino)-4-methylphenol and 2,4-dichloro-3-aminophenol, o-aminophenol and derivatives thereof, m-diaminobenzene and derivatives thereof, such as, for example, 2,4-diaminophenoxyethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2-hydroxyethylamino)-1-methylbenzene and 1-amino-3-bis(2'-hydroxyethyl)aminobenzene, o-diaminobenzene and derivatives thereof, such as, for example, 3,4-diaminobenzoic acid and 2,3-diamino-1-methylbenzene, di- or trihydroxybenzene derivatives, such as, for example, resorcinol, resorcinolmonomethyl ether, 2-methylresorcinol, 5-methylresorcinol, 2,5-dimethylresorcinol, 2-chlororesorcinol, 4-chlororesorcinol, pyrogallol and 1,2,4-trihydroxybenzene, pyridine derivatives, such as, for example, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine and 3,5-diamino-2,6-dimethoxypyridine, naphthalene derivatives, such as, for example, 1-naphthol, 2-methyl-1-naphthol, 2-hydroxymethyl-1-naphthol, 2-hydroxyethyl-1-naphthol, 1,5-dihydroxynaphthalene, 1,6-dihydroxynaphthalene, 1,7-dihydroxynaphthaiene, 1,8-dihydroxynaphthalene, 2,7-dihydroxynaphthalene and 2,3-dihydroxynaphthalene, morpholine derivatives, such as, for example, 6-hydroxybenzomorpholine and 6-aminobenzomorpholine, quinoxaline derivatives, such as, for example, 6-methyl-1,2,3,4-tetrahydroquinoxaline, pyrazole derivatives, such as, for example, 1-phenyl-3-methylpyrazol-5-one, indole derivatives, such as, for example, 4-hydroxyindole, 6-hydroxyindole and 7-hydroxyindole, methylenedioxybenzene derivatives, such as, for example, 1-hydroxy-3,4-methylenedioxybenzene, 1-amino-3,4-methylenedioxybenzene and 1-(2'-hydroxyethyl)amino-3,4-methylenedioxybenzene.

Particularly suitable coupler components are 1-naphthol, 1,5-, 2,7- and 1,7-dihydroxynaphthalene, 3-aminophenol, 5-amino-2-methylphenol, 2-amino-3-hydroxypyridine, resorcinol, 4-chlororesorcinol, 2-chloro-6-methyl-3-aminophenol, 2-methylresorcinol, 5-methylresorcinol, 2,5-dimethylresorcinol and 2,6-dihydroxy-3,4-dimethylpyridine.

Direct dyes are usually nitrophenylenediamines, nitroaminophenols, azo dyes, anthraquinones or indophenols. Particularly suitable direct dyes are the compounds known under the international names or trade names HC Yellow 2, HC Yellow 4, HC Yellow 5, HC Yellow 6, Basic Yellow 57, Disperse Orange 3, HC Red 3, HC Red BN, Basic Red 76, HC Blue 2, HC Blue 12, Disperse Blue 3, Basic Blue 99, HC Violet 1, Disperse Violet 1, Disperse Violet 4, Disperse Black 9, Basic Brown 16 and Basic Brown 17, and 1,4-bis(β-hydroxyethyl)amino-2-nitrobenzene, 4-amino-2-nitrodiphenylamine-2'-carboxylic acid, 6-nitro-1,2,3,4-tetrahydroquinoxaline, hydroxyethyl-2-nitrotoluidine, picramic acid, 2-amino-6-chloro-4-nitrophenol, 4-ethylamino-3-nitrobenzoic acid and 2-chloro-6-ethylamino-1-hydroxy-4-nitrobenzene.

Naturally occurring direct dyes are, for example, henna red, henna neutral, henna black, chamomile blossom, sandalwood, black tea, buckthorn bark, sage, logwood, madder root, catechu, cedar and alkanna root.

It is not necessary for the oxidation dye precursors or the direct dyes to each represent uniform compounds. Rather, it is possible that, as a result of the preparation processes for the individual dyes, further components are present in minor amounts in the hair colorants according to the invention, provided that these do not adversely affect the coloring result, or have to be excluded for other reasons, e.g. toxicological reasons.

With regard to the dyes which can be used in the hair colorants and tints according to the invention, reference is also made expressly to the monograph by Ch. Zviak, The Science of Hair Care, chapter 7 (pages 248–250; direct dyes), and chapter 8, pages 264–267; oxidation dye precursors), published as volume 7 of the series "Dermatology" (Ed. Ch., Culnan and H. Maibach), Verlag Marcel Dekker Inc., New York, Basle, 1986, and the "European Inventory of Cosmetic Raw Materials", published by the European Commission, available in diskette format from the Bundesverband Deutscher Industrie- und Handelsunternehmen für Arzneimittel, Reformwaren und Körperpflegemittel e.V., Mannheim.

The precursors of nature-analogous dyes used are, for example, indoles and indolines, and their physiologically compatible salts. Preference is given to those indoles and indolines which have at least one hydroxyl or amino group, preferably as substituent on the six-membered ring. These groups can carry further substituents, e.g. in the form of an etherification or esterification of the hydroxyl group or an alkylation of the amino group. Particularly advantageous properties are shown by 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid, 6-hydroxyindoline, 6-aminoindoline and 4-aminoindoline, and 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, 6-hydroxyindole, 6-aminoindole and 4-aminoindole.

Within this group, particular emphasis is given to N-methyl-5,6-dihydroxyindoline, N-ethyl-5,6-dihydroxyindoline, N-propyl-5,6-dihydroxyindoline, N-butyl-5,6-dihydroxyindoline and, in particular, 5,6-dihydroxyindoline and N-methyl-5,6-dihydroxyindole, N-ethyl-5,6-dihydroxyindole, N-propyl-5,6-dihydroxyindole, N-butyl-5,6-dihydroxyindole and, in particular, 5,6-dihydroxyindole.

The indoline and indole derivatives in the colorants used for the purposes of the method according to the invention [lacuna] be used either as free bases or else in the form of their physiologically compatible salts with inorganic or organic acids, e.g. the hydrochlorides, the sulfates and hydrobromides.

When using dye precursors of the indoline or indole type, it may be preferred to use these together with at least one amino acid and/or at least one oligopeptide. Preferred amino acids are aminocarboxylic acids, in particular α-aminocarboxylic acids and ω-aminocarboxylic acids. Of the α-aminocarboxylic acids, particular preference is given in turn to arginine, lysine, ornithine and histidine. A very particularly preferred amino acid is arginine, in particular in free form, but also used as the hydrochloride.

Hair colorants, particularly if the coloration is carried out oxidatively, whether with atmospheric oxygen or other oxidizing agents such as hydrogen peroxide, are usually adjusted to be slightly acidic to alkaline, i.e. to pH values in the range from about 5 to 11. For this purpose, the colorants comprise alkalinizing agents, usually alkali metal or alkaline earth metal hydroxides, ammonia or organic amines. Preferred alkalinizing agents are monoethanolamine, monoisopropanolamine, 2-amino-2-methylpropanol, 2-amino-2-methyl-1,3-propanediol, 2-amino-2-ethyl-1,3-propanediol, 2-amino-2-methylbutanol and triethanolamine, and also alkali metal and alkaline earth metal hydroxides. In particular, monoethanolamine, triethanolamine and 2-amino-2-methylpropanol and 2-amino-2-methyl-1,3-propanediol are preferred within this group. The use of ω-amino acids, such as ω-aminocaproic acid, as alkalinizing agent is also possible.

If the actual hair colors are formed in the course of an oxidative process, then customary oxidizing agents, such as, in particular, hydrogen peroxide or addition products thereof onto urea, melamine or sodium borate, can be used. The oxidation with atmospheric oxygen as the sole oxidizing agent may, however, be preferred. In addition, it is possible to carry out the oxidation using enzymes, where the enzymes are used both for generating oxidizing percompounds, and also for intensifying the action of a small amount of oxidizing agents present, or else enzymes are used which transfer electrons from suitable developer components (reducing agents) to atmospheric oxygen. Preference is given here to oxidases, such as tyrosinase, ascorbate oxidase and laccase, or else glucose oxidase, uricase or pyruvate oxidase. Mention may also be made of the procedure to intensify the action of small amounts (e.g. 1% and below, based on the overall agent) of hydrogen peroxide using peroxidases.

Expediently, the preparation of the oxidizing agent is then mixed directly prior to coloring the hair with the preparation containing the dye precursors. The ready-to-use hair-coloring preparation formed here should preferably have a pH in the range from 6 to 10. Particular preference is given to application of the hair colorants in a weakly alkaline medium. The application temperatures can be in a range between 15 and 40° C., preferably at the temperature of the scalp. After a contact time of about 5 to 45, in particular 15 to 30, minutes, the hair colorant is removed from the hair to be colored by rinsing out. Afterwashing with a shampoo is dispensed with if a strongly surfactant-containing carrier, e.g. a color shampoo, has been used.

Particularly in the case of hair which is difficult to color, the preparation containing the dye precursors can be applied to the hair without prior mixing with the oxidation component. Then, after a contact time of from 20 to 30 minutes—optionally after interim rinsing—the oxidation component is applied. After a further contact time of from 10 to 20 minutes, the hair is then rinsed and, if desired, after-shampooed. In this embodiment, according to a first variant in which the prior application of the dye precursors is thought to effect better penetration into the hair, the corresponding agent is adjusted to a pH of about 4 to 7. According to a second variant, an air oxidation is firstly attempted, where the applied agent preferably has a pH of from 7 to 10. In the case of subsequent accelerated post-oxidation, the use of peroxydisulfate solutions which have been made acidic as oxidizing agents may be preferred.

In addition, the development of the coloration can be supported and increased by adding certain metal ions to the agent. Such metal ions are, for example, $Zn^{2+}$, $Cu^{2+}$, $Fe^{2+}$, $Fe^{3+}$, $Mn^{2+}$, $Mn^{4+}$, Li+, $Mg^{2+}$, $Ca^{2+}$ and $Al^{3+}$. Particularly suitable in this connection are $Zn^{2+}$, $Cu^{2+}$ and $Mn^{2+}$. The metal ions can in principle be used in the form of any desired physiologically compatible salt. Preferred salts are the acetates, sulfates, halides, lactates and tartrates. By using these metal salts, it is possible both to accelerate the development of the coloration and also to influence the color nuance in a targeted manner.

The active ingredient according to the invention can also be used in products for the cleaning of surfaces such as glass, porcelain, plastic, textiles, leather, surface coatings or wood. The active ingredient is particularly suitable, for example, for use in manual and machine dishwashing detergents, glass cleaners, bathroom and toilet cleaners, and also floor cleaners and floorcare compositions.

EXAMPLES

Unless noted otherwise, all amounts are parts by weight.

1. Deodorant Roll-on

| Constituent | Chemical name | INCI name | % by wt. |
|---|---|---|---|
| Methocel ® E4M Premium EP (DOW) | Hydroxy-propylmethyl-cellulose | Hydroxy-propylmethyl-cellulose | 0.8 |
| Water | | | 49.2 |
| HYDAGEN ® HCMF (Cognis) | Chitosan | Chitosan | 0.2 |
| Glycolic acid (Merck) | Glycolic acid | Glycolic acid | 0.08 |
| Water | | | ad 100 |
| Ethanol | | | 25.0 |
| 2,5-Dihydro-5-methoxy-2-furanone | | | 0.5 |
| CETIOL ® HE (Cognis) | Polyol fatty acid ester | PEG-7-glyceryl cocoate | 3.0 |

2. Deodorant Pump Spray

| Constituent | Chemical name | INCI declaration | % by wt. |
|---|---|---|---|
| Ethanol | | | 40.0 |
| HYDAGEN ® C.A.T. | Triethyl citrate | Triethyl citrate | 2.0 |
| Water | | | ad 100 |
| Tetrahydro-5-oxo-2-furanecarboxylic acid | | | 3.0 |
| HYDAGEN ® DCMF | Chitosan | Chitosan | 0.1 |
| Glycolic acid (Merck) | | Glycolic acid | 0.04 |
| pH | | | 4.0 |

3. Aftershave Cream

| Constituent | Chemical name | INCI declaration | % by wt. |
|---|---|---|---|
| EMULGADE ® SE (Cognis) | Mixture of partial glycerides, fatty alcohols, wax esters and ethoxylated fatty alcohols | Glyceryl Stearate (and) Ceteareth-20 (and) Ceteareth-12 (and) Cetearyl Alcohol (and) Cetyl Palmitate | 4.0 |
| LANETTE ® O (Cognis) | Cetylstearyl alcohol | Cetearyl Alcohol | 1.0 |
| MYRITOL ® 312 | Caprylic/ | Caprylic/ | 3.0 |

-continued

| Constituent | Chemical name | INCI declaration | % by wt. |
|---|---|---|---|
| (Cognis) | capric tri-glyceride | Capric Triglyceride | |
| CETIOL ® PGL (Cognis) | | Hexyldecanol (and) Hexyldecyl Laurate | 7.0 |
| DC ® 190 (Dow Corning) | | Dimethicone | 0.5 |
| GLUADIN ® AGP (Cognis) | Partial hydrolyzate from wheat | Hydrolyzed Wheat Protein | 0.5 |
| Allantoin | | | 0.1 |
| Panthenol (50%) | | | 0.5 |
| Water | | | ad 100 |
| (R)-(−)-4-hydroxymethyl-γ-butyrolactone (Merck) | | | 0.3 |
| CETIOL ® PGL (Cognis) | | Hexyldecanol (and) Hexyldecyl Laurate | 1.0 |
| KOH, 20% strength | | Potassium Hydroxide | 0.5 |
| HYDAGEN ® B (Cognis) | | Bisabolol | 0.2 |
| Ethanol | | | 10.0 |

4. Moisturizing Cream Containing Vitamin E

| Constituent | Chemical name | INCI declaration | % by wt. |
|---|---|---|---|
| EMULGADE ® PL 68/50 | Mixture of alkyl polyglycoside and cetylstearyl alcohol | Cetearyl Glucoside (and) Cetearyl Alcohol | 5.0 |
| LANETTE ® E Powder (Cognis) | Sodium cetylstearyl sulfate | Sodium Cetearyl Sulfate | 0.25 |
| CUTINA ® GMS (Cognis) | Glycerol monostearate | Glyceryl Stearate | 2.0 |
| MYRITOL ® 312 (Cognis) | Caprylic/capric triglyceride | Caprylic/Capric Triglyceride | 5.0 |
| CETIOL ® LC (Cognis) | Caprylic/capric esters of saturated fatty alcohols C12–C18 | Coco-Caprylate/Caprate | 5.0 |
| EUTANOL ® G 16 (Cognis) | 2-Hexyldeconal (Guerbet alcohol) | Hexyldecanol | 2.0 |
| COPHEROL ® F 1300 (Cognis) | RRR-(α)-Tocopherol | Tocopherol | 1.0 |
| Wacker silicone oil AK 350 (Wacker) | | Dimethicone | 0.5 |
| (S)-(+)-4-hydroxymethyl-γ-butyrolactone (Merck) | | | 1.5 |
| Glycerol 86% | | Glycerin | 3.0 |
| D-Panthenol USP | | | 0.5 |
| Water | | | ad 100 |
| Viscosity (mPas), Brook. RVF, 23° C., sp.TE, 4 rpm, with Helipath | | | 150 000 |

5. Rich Nightcare

| Constituent | Chemical name | INCI name | % by wt. |
|---|---|---|---|
| EMULGADE ® PL 68/50 (Cognis) | Mixture of alkyl polyglycoside and cetylstearyl alcohol | Cetearyl Glucoside (and) Cetearyl Alcohol | 3.0 |
| LANETTE ® O (Cognis) | Cetylstearyl alcohol | Cetearyl Alcohol | 4.0 |
| CETIOL ® J 600 (Cognis) | Liquid wax ester | Oleyl Erucate | 4.0 |
| CETIOL ® V (Cognis) | Decyl oleate | Decyl Oleate | 4.0 |
| CETIOL ® OE (Cognis) | Di-n-octyl ether | Dicaprylyl Ether | 4.0 |
| MYRITOL ® 318 (Cognis) | Caprylic/capric triglyceride | Caprylic/Capric Triglyceride | 3.5 |
| Baysilon ® M 350 (Bayer) | | Dimethicone | 0.5 |
| COPHEROL ® F 1300 (Cognis) | RRR-(α)-Tocopherol | Tocopherol | 1.0 |
| Water | | | ad 100 |
| Glycerol 86% | | Glycerin | 3.0 |
| Carbopol ® 981 2% strength | | Carbomer | 10.0 |
| KOH 20% | | | 0.3 |
| LIPOCUTIN ® (Cognis) | | Aqua (and) Lecithin (and) Cholesterol (and) Decetyl Phosphate | 5.0 |
| D,L-2-hydroxy-3,3-dimethyl-γ-butyrolactone | | | 2.0 |
| Viscosity (mPas), Brookfield RVF, 23° C., sp.TE, 4 rpm, with Helipath | | | 137 500 |

6. All-purpose Cream

| Constituent | Chemical name | INCI name | % by wt. |
|---|---|---|---|
| DEHYMULS ® PGPH (Cognis) | Polyglycerol poly-12-hydroxy-stearate | Polyglyceryl poly-12-hydroxy-stearate | 4.5 |
| MYRITOL ® 331 (Cognis) | | Cocoglycerides | 5.0 |
| CETIOL ® OE (Cognis) | Di-n-octyl ether | Dicaprylyl Ether | 5.0 |
| Tetrahydro-5-oxo-2-furanecarboxylic acid | | | 1.0 |
| Zinc stearate (Bärlocher) | | Zinc stearate | 1.0 |
| Glycerol (86%) | | Glycerin | 5.0 |
| MgSO$_4$.7H$_2$O | | | 0.5 |
| Water | | | ad 100 |
| Viscosity (mPas), Brookfield RVF, 23° C., spindle TE, 4 rpm, with Helipath | | | ca. 200 000 |

7. Rich W/O Cream

| Constituent | Chemical name | INCI name | % by wt. |
|---|---|---|---|
| DEHYMULS ® PGPH (Cognis) | Polyglycerol poly-12-hydroxy-stearate | Polyglyceryl poly-12-hydroxy-stearate | 3.0 |
| LAMEFORM ® TGI (Cognis) | Triglycerol diisostearate | Polyglyceryl-3-Diisostearate | 3.0 |

-continued

| Constituent | Chemical name | INCI name | % by wt. |
|---|---|---|---|
| Beeswax 8100 (Kahl & Co.) | Beeswax | Cera Alba | 3.0 |
| Zincum ® N 29 (Bärlocher) | Zinc stearate | Zinc Stearate | 1.0 |
| CETIOL ® OE (Cognis) | Di-n-octyl ether | Dicaprylyl Ether | 3.0 |
| CETIOL ® LC (Cognis) | Caprylic/capric esters of saturated fatty alcohols C12–C18 | Coco Caprylate/ Caprate | 6.0 |
| MYRITOL ® 312 (Cognis) | Caprylic/capric triglyceride | Caprylic/ Capric Triglyceride | 8.0 |
| Almond Oil | Almond oil | Almond Oil | 8.0 |
| Dihydro-3-hydroxy-4,4-dimethyl-2(3H)-furanone | | | 1.0 |
| COPHEROL ® F 1300 (Cognis) | RRR-(α)-Tocopherol | Tocopherol | 1.0 |
| Glycerol | | Glycerin | 5.0 |
| $MgSO_4 \times 7H_2O$ | | | 1.0 |
| Water | | | ad 100 |
| Viscosity (mPas), Brookfield, RVF, 23° C., spindle TE, 4 rpm, with Helipath | | | 150 000 |

8. Natural Tinting Day Cream

| Constituent | Chemical name | INCI name | % by wt. |
|---|---|---|---|
| EMULGADE ® SE (Cognis) | Mixture of partial glycerides, fatty alcohols, wax esters and ethoxylated fatty alcohols | Glyceryl Stearate (and) Ceteareth-20 (and) Ceteareth-12 (and) Cetearyl Alcohol (and) Cetyl Palmitate | 6.0 |
| CUTINA ® MD (Cognis) | Mixture of mono- and diglycerides of palmitic and stearic acid | Glyceryl Stearate | 2.0 |
| CETIOL ® MM (Cognis) | Myristyl myristate | Myristyl Myristate | 1.0 |
| MYRITOL ® 312 (Cognis) | Caprylic/capric triglyceride | Caprylic/ Capric Triglyceride | 5.0 |
| CETIOL ® SN (Cognis) | Ester of a branched fatty acid with saturated fatty alcohols C16–C18 | Cetearyl Isononanoate | 5.0 |
| CETIOL ® OE (Cognis) | Di-n-octyl ether | Dicaprylyl Ether | 5.0 |
| Grape Seed Oil | | Grape Seed Oil | 0.5 |
| Copherol ® 1250 (Cognis) | RRR-(α)-Tocopheryl acetate | Tocopheryl Acetate | 1.0 |
| D,L-3,3-Dimethyl-2-hydroxy-γ-butyrolactone | | | 2.0 |
| Eusolex ® 8020 (Merck) | | 4 Isopropyl dibenzoyl-methane | 1.0 |
| Vitamin A palmitate | | | 0.2 |
| Titanium dioxide | | | 1.0 |
| Talc | | | 1.0 |
| Glycerol 86% strength | | Glycerin | 5.0 |
| Water | | | ad 100 |
| KOH, 20% strength | | Potassium Hydroxide | 0.3 |
| Viscosity (mPas)/Brookfield, RVF, 23° C., spindle TE, 4 rpm, with Helipath | | | 287 500 |
| pH | | | 6–7 |

9. Lipstick

| Constituent | Chemical name | INCI name | % by wt. |
|---|---|---|---|
| MYRITOL ® 318 (Cognis) | Caprylic/capric triglyceride | Caprylic/ Capric Triglyceride | 14.0 |
| MYRITOL ® PC (Cognis) | Propylene glycol octanoate/ decanoate | Propylene Glycol Dicaprylate/ Dicaprate | 6.0 |
| EUTANOL ® G (Cognis) | 2-Octyldodec-anol (Guerbet alcohol) | Octyldodecanol | 17.0 |
| Candelilla Wax | | Candelilla cera | 7.0 |
| Carnauba Wax | | Carnauba cera | 5.5 |
| Beeswax 8100 (Kahl) | | Cera alba | 6.5 |
| GENEROL ® 122 N (Cognis) | Refined soy-bean sterol | Soybean (Glycine Soya) Sterol | 2.5 |
| MONOMULS ® 90 L 12 (Cognis) | Molecularly distilled lauric acid monoglyceride | Glyceryl Laurate | 3.0 |
| DEHYMULS ® PGPH (Cognis) | Polyglycerol poly-12-hydroxy-stearate | Polyglyceryl-2 Dipolyhy-droxy-stearate | 4.0 |
| Castor oil | | Ricinus communis | 18.0 |
| 4-Hydroxy-2,5-dimethyl-3(2H)-furanone | | | 1.0 |
| Color pigments | | | 2.0 |
| HYDAGEN ® CMF (Cognis) | Chitosan solution | Chitosan Glycolate | 10.0 |
| COPHEROL ® F 1300 (Cognis) | RRR-(α)-Tocopherol | Tocopherol | 2.0 |

10. Cold-wave Neutralizer

| Constituent | Chemical name | INCI name | % by wt. |
|---|---|---|---|
| DEHYTON ® K (Cognis) | True betaine. Fatty acid amide derivative with betaine structure (ca. 32%) | Cocamidopro-pyl Betaine | 6.0 |
| NUTRILAN ® H (Cognis) | Protein partial hydrolyzate (ca. 36%) | Hydrolyzed Collagen | 5.0 |
| LAMEQUAT ® L (Cognis) | Cationized protein hydrolyzate (ca. 36%) | Laurdimonium Hydroxypropyl Hydrolyzed Collagen | 3.0 |
| Hydrogen peroxide 35% strength | | | 7.5 |
| Keltrol T (1% swelling) | | Xanthan Gum | 15.0 |
| Water | | | ad 100 |

-continued

| Constituent | Chemical name | INCI name | % by wt. |
|---|---|---|---|
| S(+)-2-Hydroxy-3,3-dimethyl-γ-butyrolactone (Aldrich) | | | 1.0 |
| pH | | | 3.5 |

11. Cold-wave Neutralizer, in Emulsion Form

| Constituent | Chemical name | INCI name | % by wt. |
|---|---|---|---|
| DEHYQUART ® C 4046 (Cognis) | Mixture of ester quat, fatty alcohol and nonionic emulsifier | Cetearyl Alcohol (and) Dipalmitoylethyl Hydroxyethylmonium Methosulfate (and) Ceteareth-20 | 3.0 |
| Water | | | ad 100 |
| TURPINAL ® SL (Cognis) | | Etidronic Acid | 0.3 |
| Hydrogen peroxide (35%) | | Hydrogen Peroxide | 7.5 |
| PLANTACARE ® 2000 UP (Cognis) | C8–C16 fatty alcohol glycoside | Decyl Glucoside | 1.0 |
| D,L-2-Hydroxy-3,3-dimethyl-γ-butyrolactone (Aldrich) | | | 0.5 |
| pH | | | 2.7 |
| Viscosity (mPas), Brookfield RVT, 23° C., sp. TC, 10 rpm | | | 3600 |

12. Sprayable Hair Treatment, Leave-on

| Constituent | Chemical name | INCI name | % by wt. |
|---|---|---|---|
| MONOMULS ® 60–35 C (Cognis) | Hydrogenated palm glycerides | Hydrogenated Palm Glycerides | 1.24 |
| EUMULGIN ® B1 (Cognis) | Polyoxyethylene-12 cetylstearyl alcohol | Ceteareth-12 | 2.76 |
| CETIOL ® S (Cognis) | Hydrocarbon | Dioctylcyclohexane | 9.0 |
| CETIOL ® OE (Cognis) | Di-n-octyl ether | Dicaprylyl Ether | 9.0 |
| Dow Corning DC 345 ® (Dow Corning) | | Cyclomethicone | 2.0 |
| 2,5-Dihydro-5-methoxy-2-furanone (Merck) | | | 2.0 |
| Water | | | ad 100 |
| GLUADIN ® WQ (Cognis) | Cationized wheat protein hydrolyzate (ca. 31%) | Laurdimonium Hydroxypropyl Hydrolyzed Wheat Protein | 2.85 |
| PLANTACARE ® 2000 UP (Cognis) | C8–C16 fatty alcohol glycoside (ca. 50%) | Decyl Glucoside | 1.00 |
| Viscosity mPas | | | <100 |

13. Leave-on Hair Treatment

| Constituent | Chemical name | INCI name | % by wt. |
|---|---|---|---|
| DEHYQUART ® F 75 (Cognis) | Mixture of ester quat and fatty alcohol | Distearoylethyl Hydroxyethylmonium Methosulfate (and) Cetearyl Alcohol | 0.7 |
| DEHYMULS ® PGPH (Cognis) | Polyglycerol poly-12-hydroxystearate | Polyglyceryl-2 Dipolyhydroxystearate | 1.0 |
| LANETTE ® O (Cognis) | Cetylstearyl alcohol | Cetearyl Alcohol | 3.0 |
| EUTANOL ® G (Cognis) | 2-Octyldodecanol (Guerbet alcohol) | Octyldodecanol | 0.2 |
| CETIOL ® J 600 (Cognis) | Liquid wax ester | Oleyl Erucate | 0.1 |
| PLANTACARE ® 1200 UP (Cognis) | C12–C16 fatty alcohol glycoside (ca. 50%) | Lauryl Glucoside | 2.5 |
| 4-Hydroxy-2,5-dimethyl-3(2H)-furanone | | | 1.0 |
| Water | | | ad 100 |
| GLUADIN ® W 40 (Cognis) | Partial hydrolyzate from wheat (ca. 40%) | Hydrolyzed Wheat Protein | 2.0 |
| Panthenol (50%) | | | 0.7 |
| pH | | | 4 |
| Viscosity (mPas)/Brookfield, RVF 23° C., spindle 5, 10 rpm | | | 6800 |

14. Leave-on Hair Treatment

| Constituent | Chemical name | INCI name | % by wt. |
|---|---|---|---|
| Sepigel ® 305 (Seppic) | | Polyacrylamide (and) C13–14 Isoparaffin (and) Laureth-7 | 3.0 |
| COMPERLAN ® KD (Cognis) | Coconut fatty acid diethanolamide | Cocamide DEA | 2.0 |
| Dihydro-3-hydroxy-4,4-dimethyl-2(3H)-furanone (Aldrich) | | | 3.0 |
| Water | | | ad 100 |
| PLANTACARE ® 1200 UP (Cognis) | C12–C16 fatty alcohol glycoside (ca. 50%) | Lauryl Glucoside | 0.5 |
| CETIOL ® J 600 (Cognis) | Liquid wax ester | Oleyl Erucate | 0.5 |
| COPHEROL ® 1250 (Cognis) | RRR-(α)-Tocopheryl acetate | Tocopherol | 0.2 |
| GLUADIN ® ALMOND (Cognis) | Partial hydrolyzate from almonds (ca. 22%) | Hydrolyzed Sweet Almond Protein | 3.0 |
| GLUADIN ® WQ (Cognis) | Cationized wheat protein hydrolyzate (ca. 31%) | Laurdimonium Hydroxypropyl Hydrolyzed Wheat Protein | 0.8 |

-continued

| Constituent | Chemical name | INCI name | % by wt. |
|---|---|---|---|
| Ethanol | | | 10.0 |
| pH | | | 7 |
| Viscosity (mPas)/Brookfield RVF, 23° C., spindle 4, 10 rpm | | | 6700 |

15. Hair Rinse

| Constituent | Chemical name | INCI name | % by wt. |
|---|---|---|---|
| DEHYQUART ® C 4046 (Cognis) | Mixture of ester quat, fatty alcohol and nonionic emulsifier | Cetearyl Alcohol (and) Dipalmitoylethyl Hydroxyethyl-monium Metho-sulfate (and) Ceteareth20 | 4.0 |
| CETIOL ® SN (Cognis) | Ester of a branched fatty acid with saturated fatty alcohols C16–C18 | Cetearyl Isononanoate | 1.0 |
| GLUADIN ® ALMOND (Cognis) | Partial hydrolyzate from almonds (ca. 22%) | Hydrolyzed Sweet Almond Protein | 2.1 |
| Dihydro-3-hydroxy-4,4-dimethyl-2(3H)-furanone (Aldrich) | | | 1.5 |
| Water | | | ad 100 |
| pH | | | 3.5 |
| Viscosity (mPas)/Brookfield RVF, 23° C., spindle 4, 10 rpm | | | 4000 |

16. Hair Treatment

| Constituent | Chemical name | INCI name | % by wt. |
|---|---|---|---|
| Dehyquart ® L 80 (Cognis) | Mixture of ester quat and propylene glycol (ca. 75%) | Dicocoylethyl Hydroxyethyl-monium Metho-sulfate (and) Propylene Glycol | 0.9 |
| LANETTE ® O (Cognis) | Cetylstearyl alcohol | Cetearyl Alcohol | 3.5 |
| MONOMULS ® 60–35 C (Cognis) | Hydrogenated palm glycerides | Hydrogenated Palm Glycerides | 1.0 |
| EUMULGIN ® B 2 (Cognis) | Polyoxyethylene-20 cetylstearyl alcohol | Ceteareth-20 | 0.8 |
| COSMEDIA ® GUAR C 261 (Cognis) | Guar hydroxy-propyltrimethyl-ammonium chloride | Guar Hydroxy-propyl Trimonium Chloride | 0.3 |
| Tetrahydro-5-oxo-2-furanecarboxylic acid, Na salt | | | 2.0 |
| Water | | | ad 100 |
| pH | | | 3.5 |

17. Hair Mask

| Constituent | Chemical name | INCI name | % by wt. |
|---|---|---|---|
| DEHYQUART ® F 75 (Cognis) | Mixture of ester quat and fatty alcohol | Distearoylethyl Hydroxyethyl-monium Methosulfate (and) Cetearyl Alcohol | 3.0 |
| LANETTE ® O (Cognis) | Cetylstearyl alcohol | Cetearyl Alcohol | 4.0 |
| CUTINA ® GMS (Cognis) | Glycerol monostearate | Glyceryl Stearate | 1.0 |
| EUMULGIN ® B 2 (Cognis) | Polyoxyethylene-20 cetylstearyl alcohol | Ceteareth-20 | 1.5 |
| 4-Hydroxy-2,5-dimethyl-3(2H)-furanone | | | 2.0 |
| NUTRILAN ® KERATIN W (Cognis) | Partial hydrolyzate from keratin (ca. 20%) | Hydrolyzed Keratin | 5.0 |
| Panthenol | | | 0.8 |
| Aloe Vera Gel | | | 2.0 |
| Water | | | ad 100 |
| pH | | | 3–4 |

18. Intensive Hair Treatment

| Constituent | Chemical name | INCI name | % by wt. |
|---|---|---|---|
| DEHYQUART ® L 80 (Cognis) | Mixture of ester quat and propylene glycol (ca. 75%) | Dicocoylethyl Hydroxyethyl-monium Metho-sulfate (and) Propylene Glycol | 2.5 |
| CUTINA ® GMS (Cognis) | Glycerol monostearate | Glyceryl Stearate | 0.5 |
| LANETTE ® O (Cognis) | Cetylstearyl alcohol | Cetearyl Alcohol | 4.0 |
| HYDAGEN ® HSP (Cognis) | | Trimethylol-propane Hydroxy-methylstearate Ether | 0.5 |
| Dihydro-3-hydroxy-4,4-dimethyl-2(3H)-furanone (Aldrich) | | | 3.0 |
| LAMESOFT ® PO 65 (Cognis) | Mixture of alkyl polyglycoside and fatty acid monoglyceride | Coco-Glucoside (and) Glyceryl Oleate | 2.5 |
| Water | | | ad 100 |
| pH | | | 3.5 |
| Viscosity (mPas), Brook. RVF, 23° C., spindle 4, 10 rpm | | | 4400 |

19. Hair Ends Fluid

| Constituent | Chemical name | INCI name | % by wt. |
|---|---|---|---|
| HYDAGEN ® HCMF (Cognis) | Chitosan powder | Chitosan | 0.4 |
| Glycolic acid (Merck) | | Glycolic acid | 0.2 |
| Glycerol 86% | | Glycerin | 55.0 |
| Tylose ® H 100.000 | | | 0.4 |

-continued

| Constituent | Chemical name | INCI name | % by wt. |
|---|---|---|---|
| YP (Hoechst) R-(−)-2-Hydroxy-3,3-dimethyl-γ-butyrolactone (Aldrich) | | | 3.0 |
| GLUADIN ® R (Cognis) | Partial hydrolyzate from rice (ca. 27%) | Hydrolyzed Rice Protein (and) Hydrolyzed Vegetable Protein | 4.0 |
| Panthenol 50% | | | 1.0 |
| Ethanol | | | 10.0 |
| Water | | | ad 100 |
| pH | | 4.5 | |

20. Leave-on Hair Milk

| Constituent | Chemical name | INCI name | % by wt. |
|---|---|---|---|
| DEHYQUART ® L 80 (Cognis) | Mixture of brighteners and propylene glycol (ca. 75%) | Dicocoylethyl Hydroxyethyl-monium Metho-sulfate (and) Propylene Glycol | 2.0 |
| LAMESOFT ® PO 65 (Cognis) | Mixture of alkyl polyglycoside and fatty acid monoglyceride | Coco Glucoside (and) Glyceryl Oleate | 2.0 |
| Tetrahydro-5-oxo-2-furanecarboxylic acid, K salt | | | 2.0 |
| Water | | | ad 100 |
| pH | | 3.5 | |

21. Pump Spray Setting Composition

| Constituent | Chemical name | INCI name | % by wt. |
|---|---|---|---|
| HYDAGEN ® HCMF (Cognis) | Chitosan powder | Chitosan | 1.0 |
| Glycolic acid (Merck) | | | 0.4 |
| 2,5-Dihydro-5-methoxy-2-furanone (Merck) | | | 0.5 |
| PLANTACARE ® 1200 UP (Cognis) | C12–C16 fatty alcohol glycoside (ca. 50%) | Lauryl Glucoside | 0.2 |
| GLUADIN ® WQ (Cognis) | Cationized wheat protein hydrolyzate | Laurdimonium Hydroxypropyl Hydrolyzed Wheat Protein | 1.0 |
| Ethanol | | | 40.0 |
| Water | | | ad 100 |
| pH | | 4.0 | |

22. Setting Foam

| Constituent | Chemical name | INCI name | % by wt. |
|---|---|---|---|
| HYDAGEN ® HCMF (Cognis) | Chitosan powder | Chitosan | 0.4 |
| Glycolic acid (Merck) | | glycolic acid | 0.2 |
| Dihydro-3-hydroxy-4,4-dimethyl-2 (3H)-furanone (Aldrich) | | | 1.0 |
| DEHYQUART ® A (Cognis) | Cetyltrimethyl-ammonium chloride (ca. 25%) | Cetrimonium Chloride | 1.0 |
| GLUADIN ® W 40 (Cognis) | Partial hydrolyzate from wheat (ca. 40%) | Hydrolyzed Wheat Protein | 2.0 |
| Water | | | ad 100 |

23. Styling Wax

| Constituent | Chemical name | INCI name | % by wt. |
|---|---|---|---|
| CUTINA ® MD (Cognis) | Mixture of mono- and diglycerides of palmitic and stearic acid | Glyceryl Stearate | 5.0 |
| EUMULGIN ® B 1 (Cognis) | Polyoxyethylene-12 cetylstearyl alcohol | Ceteareth-12 | 1.0 |
| CETIOL ® V (Cognis) | Decyl oleate | Decyl Oleate | 5.0 |
| Paraffin oil | | | 10.0 |
| HYDAGEN ® HCMF (Cognis) | Chitosan powder | Chitosan | 0.8 |
| Glycolic acid (Merck) | | | 0.4 |
| D,L-4-Hydroxy-methyl-γ-butyro-lactone (Merck) | | | 1.0 |
| Water | | | ad 100 |

24. 2-in-1 Shampoo

| Constituent | Chemical name | INCI name | % by wt. |
|---|---|---|---|
| TEXAPON ® N 70 (Cognis) | Sodium lauryl ether sulfate with 2 mol of EO (ca. 70%) | Sodium Laureth Sulfate | 12.0 |

-continued

| Constituent | Chemical name | INCI name | % by wt. |
|---|---|---|---|
| DEHYTON ® PK 45 (Cognis) | Fatty acid amide derivative with betaine structure (ca. 45%) | Cocamidopropyl Betaine | 2.5 |
| PLANTACARE ® 818 UP (Cognis) | C8–C16 fatty alcohol glycoside (ca. 50%) | Coco Glucoside | 3.0 |
| LAMESOFT ® PO 65 (Cognis) | Cocoglucoside (and) glyceryl oleate | Coco Glucoside (and) Glyceryl Oleate | 3.0 |
| COSMEDIA ® GUAR C 261 N (Cognis) | Guar hydroxypropyltrimethylammonium chloride | Guar Hydroxypropyl Trimonium Chloride | 0.3 |
| EUPERLAN ® PK 1200 (Cognis) | Liquid dispersion of pearlescence-imparting substances and auxiliaries | Coco Glucoside (and) Glycol Distearate (and) Glycerin | 5.0 |
| Sodium chloride | | | 1.2 |
| D,L-4-Hydroxymethyl-γ-butyrolactone (Merck) | | | 0.3 |
| Euxyl ® K 400 (Schülke & Mayr) | | | 0.1 |
| Water | | | ad 100 |
| pH | | 5.5 | |
| Viscosity (mPas), Brookfield RFT, 23° C., sp.4, 10 rpm | | 6300 | |

25. Conditioning Shampoo

| Constituent | Chemical name | INCI name | % by wt. |
|---|---|---|---|
| TEXAPON ® N 70 (Cognis) | Sodium lauryl ether sulfate with 2 mol of EO (ca. 70%) | Sodium Laureth Sulfate | 10.0 |
| PLANTACARE ® 818 UP (Cognis) | C8–C16 fatty alcohol glycoside (ca. 50%) | Coco Glucoside | 4.0 |
| DEHYTON ® K (Cognis) | Fatty acid amide derivative with betaine structure (ca. 30%) | Cocamidopropyl Betaine | 5.0 |
| LAMESOFT ® PO 65 (Cognis) | Cocoglucoside (and) glyceryl oleate | Coco Glucoside (and) Glyceryl Oleate | 1.5 |
| EUPERLAN ® PK 3000 AM (Cognis) | Liquid dispersion of pearlescence-imparting substances and amphoteric surfactant | Glycol Distearate (and) Laureth 4 (and) Cocamidopropyl Betaine | 3.2 |
| Dihydro-3-hydroxy-4,4-dimethyl-2(3H)-furanone (Aldrich) | | | 1.5 |
| Polymer JR ® 400 (Amerchol) | | Polyquaternium 10 | 0.3 |
| Sodium Chloride | | | 1.5 |
| Water | | | ad 100 |
| pH | | 5.5 | |
| Viscosity (mPas), Brookfield RVF, 23° C., spindle 4, 10 rpm | | 8500 | |

26. Baby Shampoo

| Constituent | Chemical name | INCI name | % by wt. |
|---|---|---|---|
| Water | | | ad 100 |
| Polymer ® JR 400 (Amerchol) | | Polyquaternium-10 | 0.4 |
| TEXAPON ® K 14 S Special 70% (Cognis) | Sodium lauryl myristyl ether sulfate (ca. 70%) | Sodium Myreth Sulfate | 11.0 |
| DEHYTON ® PK 45 (Cognis) | Fatty acid amide derivative with betaine structure (ca. 45%) | Cocamidopropyl Betaine | 5.0 |
| PLANTACARE ® 818 UP (Cognis) | C8–C16 fatty alcohol glycoside (ca. 50%) | Coco Glucoside | 5.0 |
| LAMESOFT ® PO 65 (Cognis) | Coco-glucoside (and) glyceryl oleate | Coco Glucoside (and) Glyceryl Oleate | 5.0 |
| Euxyl ® K 400 (Schülke & Mayr) | 1,2-Dibromocyanobutane and 2-phenoxyethanol | | 0.1 |
| Sodium chloride | | | 1.8 |
| pH | | 5.5 | |
| Viscosity (mPas), Brookfield RVF, 23° C., spindle 4, 10 rpm | | 3900 | |

27. Pearlescent Care Shampoo

| Constituent | Chemical name | INCI name | % by wt. |
|---|---|---|---|
| TEXAPON ® NSO (Cognis) | Sodium lauryl ether sulfate (ca. 28%) | Sodium Laureth Sulfate | 29.0 |
| PLANTACARE ® 818 | C8–C16 fatty | Coco Glucoside | 5.0 |

-continued

| Constituent | Chemical name | INCI name | % by wt. |
|---|---|---|---|
| UP (Cognis) | alcohol glycoside (ca. 50%) | | |
| TEXAPON ® SB 3 KC (Cognis) | Sulfosuccinic half-ester based on an alkylpoly-glycol ether, di-Na salt (ca. 40%) | Disodium Laureth Sulfosuccinate | 3.8 |
| HYDAGEN ® HSP (Cognis) | | Trimethylol-propane Hydroxy-methylstearate Ether | 0.5 |
| EUPERLAN ® PK 3000 AM (Cognis) | Liquid dispersion of pearlescence-imparting substances and amphoteric surfactant | Glycol Distearate (and) Laureth-4 (and) Cocamidopropyl Betaine | 3.0 |
| NaCl | | | 2.0 |
| Water | | | ad 100 |
| pH | | | 5.5 |
| Viscosity (mPas), Brook.RVF, 23° C., spindle 4, 10 rpm | | | 4100 |

28. Cream Hair Color

| Constituent | Chemical name | INCI name | % by wt. |
|---|---|---|---|
| Lanette ® O (Cognis) | Cetylstearyl alcohol | Cetearyl Alcohol | 17.0 |
| CUTINA ® AGS (Cognis) | Ethylene glycol distearate | Glycol Distearate | 1.5 |
| EUMULGIN ® B2 (Cognis) | Polyoxyethylene-20 cetylstearyl alcohol | Ceteareth-20 | 3.0 |
| EUMULGIN ® B1 (Cognis) | Polyoxyethylene-12 cetylstearyl alcohol | Ceteareth-12 | 3.0 |
| EUMULGIN ® O5 (Cognis) | Polyoxyethylene-5 oleylcetyl alcohol | Oleth-5 | 1.0 |
| Eumulgin ® O10 (Cognis) | Polyoxyethylene-10 oleylcetyl alcohol | Oleth-10 | 1.0 |
| COMPERLAN ® KD (Cognis) | Coconut fatty acid diethanolamide | Cocamide DEA | 5.0 |
| Water | | | ad 100 |
| DEHYQUART ® L 80 (Cognis) | Mixture of ester quat and propylene glycol | Dicocoylethyl Hydroxyethyl-monium Metho-sulfate (and) Propylene Glycol | 1.5 |
| Propylene glycol | | | 5.0 |
| p-Aminophenol | | | 0.35 |
| p-Tolylenediamine | | | 0.85 |
| 2-Methylresorcinol | | | 0.14 |
| 6-Methyl-m-aminophenol | | | 0.42 |
| Dihydro-3-hydroxy-4,4-dimethyl-2(3H)-furanone (Aldrich) | | | 1.0 |
| Sodium sulfite | | | 0.6 |
| EDTA | | Tetrasodium EDTA | 0.2 |
| Ammonia, 28% | | | 5.0 |

29. Foam Bath

| Constituent | Chemical name | INCI name | % by wt. |
|---|---|---|---|
| TEXAPON ® NSO | Sodium lauryl ether sulfate (ca. 28%) | Sodium Laureth Sulfate | 27.0 |
| PLANTACARE ® 818 UP | C8–C16 fatty alcohol glycoside (ca. 50%) | Coco Glucoside | 9.0 |
| DEHYTON ® PK 45 | True betaine, fatty acid amide derivative with betaine structure (ca. 45%) | Cocamidopropyl Betaine | 4.0 |
| GLUADIN ® W 40 | Partial hydrolyzate from wheat | Hydrolyzed Wheat Protein | 4.0 |
| Dihydro-3-hydroxy-4,4-dimethyl-2(3H)-furanone (Aldrich) | | | 1.0 |
| Sodium chloride | | Sodium Chloride | 0.3 |
| Water | | | ad 100 |

30. Cleansing Milk

| Constituent | Chemical name | INCI name | % by wt. |
|---|---|---|---|
| EMULGADE ® SE (Cognis) | Mixture of partial glycerides, fatty alcohols, wax esters and ethoxylated fatty alcohols | Glyceryl Stearate (and) Ceteareth20 (and) Ceteareth12 (and) Cetearyl Alcohol (and) Cetyl Palmitate | 6.0 |
| EUTANOL ® G (Cognis) | 2-Octyldodecanol (Guerbet Alcohol) | Octyldodecanol | 7.0 |
| Dihydro-3-hydroxy-4,4-dimethyl-2(3H)-furanone (Aldrich) | | | 2.0 |
| CETIOL ® 868 (Cognis) | Isooctyl stearate | Octyl Stearate | 8.0 |
| Glycerol 86% | | Glycerin | 3.0 |
| Carbopol ® 981 (Goodrich) | | Carbomer/2% swelling | 10.0 |
| NaOH 10% | | | 0.8 |
| Water | | | ad 100 |
| Viscosity (mPas), Brookfield RVF, 23° C., spindle 5, 10 rpm | | | 8 000 |

31. All-purpose Cleaner

| Constituent | Chemical name | % by wt. |
|---|---|---|
| GLUCOPON ® 215 CS UP (Cognis) | Alkyl polyglycoside | 3.5 |
| DEHYDOL ® 04 DEO (Cognis) | Fatty alcohol ethoxylate | 1.7 |
| Citric acid | | 9.6 |
| Acetic acid | | 2.4 |
| Tetrahydro-5-oxo-2-furanecarboxylic acid | | 0.2 |
| Water | | ad 100 |
| pH | | 2.0–2.5 |

32. Hand Dishwashing Detergent

| Constituent | Chemical name | % by wt. |
| --- | --- | --- |
| C13/17-alkanesulfonate | Alkanesulfonate C13/l7 (ca. 60%) | 19.5 |
| TEXAPON ® N 70 (Cognis) | Lauryl ether sulfate, Na salt (ca. 70%) | 9.0 |
| DEHYTON ® K (Cognis) | Fatty acid amide derivative with betaine structure ca. 30 D,L-3,3-alkyl polyglucoside ca. 50% | 13.3 |
| GLUCOPON ® 600 CS UP (Cognis) | | 14.0 |
| Ethanol | | 5.0 |
| Dimethyl-2-hydroxy-γ-butyrolactone (Aldrich) | | 0.5 |
| Water | | ad 100 |
| pH | | 5–6 |

33. Fabric Softener

| Constituent | Chemical name | % by wt. |
| --- | --- | --- |
| DEHYQUART ® AU 56 | Ester quat (Cognis, ca. 80%) | 16.7 |
| Calcium chloride (25%) | | 0.5 |
| Dihydro-3-hydroxy-4,4-dimethyl-2(3H)-furanone | | 0.65 |
| Water | | ad 100 |

34. Floor Cleaner

| Constituent | Chemical name | % by wt. |
| --- | --- | --- |
| DEHYPON ® LS 54 (Cognis) | Fatty alcohol alkoxylate | 7.0 |
| DEHYPON ® LT 104 (Cognis) | Fatty alcohol alkoxylate, terminally capped | 2.0 |
| Butyl diglycol | | 10.0 |
| Na cumenesulfonate (40%) | | 3.0 |
| (R)-(–)-4-Hydroxymethyl-γ-butyrolactone | | 0.3 |
| Water | | ad 100 |
| pH | | 6.5–7.5 |

35. Hair Rinse

| | |
| --- | --- |
| Eumulgin ® B2[1] | 0.3 |
| Cetyl/stearyl alcohol | 3.3 |
| Isopropyl myristate | 0.5 |
| Paraffin oil perliquidum 15 cSt. DAB 9 | 0.3 |
| Dehyquart ® A-CA[2] | 2.0 |
| Salcare ® SC 96[3] | 1.0 |
| Citric acid | 0.4 |
| Gluadin ® WQ[4] | 2.0 |
| Dihydro-3-hydroxy-4,4-dimethyl-2(3H)-furanone | 0.5 |
| Phenonip ®[5] | 0.8 |
| Water | ad 100 |

[1]Cetylstraryl alchohol + 20 EO (INCI name: Ceteareth-20) (COGNIS)
[2]Trimethylhexadecylammonium chloride ca. 25% active subtance (INCI name: Cetrimonium Chloride) (COGNIS)
[3]N,N,N-Trimethyl-2-[(methyl-1-oxo-2-propenyl)oxy]ethaneaminium chloride monopolyer (50% active substance; INCI name: Polyquaternium-37 (and) Propylenglycol Dicaprilate Dicaprilate (and) PPG-1 Trideceth-6) (ALLIED COLLOIDS)
[4]Cationized wheat protein hydrolyzate ca. 31% active substance (INCI name: Laurdimonium Hydroxypropyl Hydrolyzed Wheat Protein) (COGNIS)
[5]Methyl hydroxybenzoate-ethyl hydroxybenzoate-propyl hydroxybenzoate-butyl hydroxybenzoate-phenoxyethanol mixture (ca. 28% active substance; INCI name: Phenoxyethanol, Methylparaben, Ethylparaben, Propylparaben, Butylparaben) (NIPA)

36. Hair Rinse

| | |
| --- | --- |
| Eumulgin ® B2 | 0.3 |
| Cetyl/stearyl alcohol | 3.3 |
| Isopropyl myristate | 0.5 |
| Paraffin oil perliquidum 15 cSt. DAB 9 | 0.3 |
| Dehyquart ® L 80[6] | 0.4 |
| Cosmedia Guar ® C 261[7] | 1.5 |
| Promois ® Milk-CAQ[8] | 3.0 |
| Dihydro-3-hydroxy-4,4-dimethyl-2(3H)-furanone | 0.5 |
| Citric acid | 0.4 |
| Phenonip ® | 0.8 |
| Water | ad 100 |

[6]Bis(cocoylethyl)hydroxyethylmethylammonium methosulfate (ca. 76% active substance in propylene glycol; INCI name: Dicocoylethyl Hydroxyethylmonium Methosulfat, Propylene Glycol) (COGNIS)
[7]Guar hydroxypropyltrimethylammonium chloride; INCI name: Guar Hydroxypropyl Trimonium Chloride (COGNIS)
[8]INCI name: Cocodimonium Hydroxypropyl Hydrolyzed Casein (SEIWA KASEI)

37. Hair Treatment

| | |
| --- | --- |
| Dehyquart ® F75[9] | 4.0 |
| Cetyl/stearyl alcohol | 4.0 |
| Paraffin oil perliquidum 15 cSt DAB 9 | 1.5 |
| Dehyquart ® A-CA | 4.0 |
| Salcare ® SC 96 | 1.5 |
| Amisafe-LMA-60 ®[10] | 1.0 |
| Gluadin ® W 20[11] | 3.0 |
| Dihydro-3-hydroxy-4,4-dimethyl-2(3H)-furanone | 0.5 |
| Citric acid | 0.15 |
| Phenonip ® | 0.8 |
| Water | ad 100 |

[9]Fatty alcohols-methyltriethanolammonium methylsulfate dialkyl ester mixture (INCI name: Distearoylethyl Hydroxyethylmonium Methosulfate, Cetearyl Alcohol) (COGNIS)
[10]INCI name Hydroxypropyl Arginine Lauryl/Myristyl Ether HCl (Ajinomoto)
[11]Wheat protein hydrolyzate (20% active substance in water; INCI name: Aqua (and) Hydrolized Wheat Protein (and) Sodium Benzoate (and) Phenoxyethanol (and) Metyhlparaben (and) Propylparaben (COGNIS)

38. Hair Treatment

| | |
| --- | --- |
| Dehyquart ® L80 | 2.0 |
| Cetyl/stearyl alcohol | 6.0 |
| Paraffin oil perliquidum 15 cSt DAB 9 | 2.0 |
| Rewoquat ® W 75[12] | 2.0 |
| Dihydro-3-hydroxy-4,4-dimethyl-2(3H)-furanone | 0.5 |
| Cosmedia Guar ® C261 | 0.5 |
| Sepigel ® 305[13] | 3.5 |
| Honeyquat ® 50[14] | 1.0 |

| | |
|---|---|
| Gluadin ® WQ | 2.5 |
| Gluadin ® W 20 | 3.0 |
| Citric acid | 0.15 |
| Phenonip ® | 0.8 |
| Water | ad 100 |

[12] 1-Methyl-2-nortallow-alkyl-3-tallow-fatty acid amidoethylimidazolinium methosulfate (ca. 75% active substance in propylene glycol; INCI name: Quaternium-27, Propylene Glycol) (WITCO)
[13] Copolymer of acrylamide and 2-acrylamido-2-methylpropanesulfonic acid (INCI name: Polyacrylamide (and) $C_{13}$–$C_{14}$Isoparaffin (and) Laureth-7) (SEPPIC)
[14] INCI name: Hydroxypropyltrimonium Honey (BROOKS)

39. Hair Treatment

| | |
|---|---|
| Dehyquart ® F75 | 0.3 |
| Salcare ® SC 96 | 5.0 |
| Gluadin ® WQ | 1.5 |
| Dow Corning ® 200 Fluid, 5 cSt[15] | 1.5 |
| Dihydro-3-hydroxy-4,4-dimethyl-2(3H)-furanone | 0.5 |
| Gafquat ® 755N[16] | 1.5 |
| Biodocarb ®[17] | 0.02 |
| Perfume oil | 0.25 |
| Water | ad 100 |

[15] Polydimethylsiloxane (INCI name: Dimethicone) (DOW CORNING)
[16] Dimethylaminoethyl methacrylate-vinylpyrrolidone copolymer, quaternized with diethyl sulfate (19% active substance in water; INCI name: Polyquaternium-11) (GAF)
[17] 3-Iodo-2-propynyl-n-butylcarbamate (INCI name: Iodopropylnyl Butylcarbamate) (MILKER & GRÜNING)

40. Hair Treatment

| | |
|---|---|
| Sepigel ® 305 | 5.0 |
| Dow Corning ® Q2-5220[18] | 1.5 |
| Promois ® Milk Q[19] | 3.0 |
| Polymer P1 corresponding to DE 3929173 | 0.6 |
| Dihydro-3-hydroxy-4,4-dimethyl-2(3H)-furanone | 0.5 |
| Genamin ® DSAC[20] | 0.3 |
| Phenonip ® | 0.8 |
| Perfume oil | 0.25 |
| Water | ad 100 |

[18] Silicone-glycol copolymer (INCI name: Dimethicone Copolyol) (DOW CORNING)
[19] INCI name Hydropropyltrimonium Hydrolyzed Casein ca. 30% active substance (SEIWA KASEI)
[20] Dimethyldistearylammonium chloride (INCI name: Distearyldimonium Chloride) (CLARIANT)

41. Shampoo

| | |
|---|---|
| Texapon ® NSO[21] | 40.0 |
| Dehyton ® G[22] | 6.0 |
| Polymer JR 400 ®[23] | 0.5 |
| Cetiol ® HE[24] | 0.5 |
| Ajidew ® NL 50[25] | 1.0 |
| Gluadin ® WQT[26] | 2.5 |
| Dihydro-3-hydroxy-4,4-dimethyl-2(3H)-furanone | 0.5 |
| Gluadin ® W 20 | 0.5 |
| Panthenol (50%) | 0.3 |
| Vitamin E | 0.1 |
| Vitamin H | 0.1 |
| Citric acid | 0.5 |
| Sodium benzoate | 0.5 |
| Perfume | 0.4 |
| NaCl | 0.5 |
| Water | ad 100 |

[21] Sodium lauryl ether sulfate ca. 28% active substance; (INCI name: Sodium Laureth Sulfate) (COGNIS)
[22] INCI name: Sodium Cocoamphoacetate ca. 30% active substance (COGNIS)
[23] Quaternized hydroxyethylcellulose (INCI name: Polyquaternium-10) (UNION CARBIDE)
[24] Polyol fatty acid ester (INCI name: PEG-7 Glyceryl Cocoate) (COGNIS)
[25] Sodium salt of 2-pyrrolodinone-5-carboxylic acid (AJINOMOTO)
[26] INCI name: Hydroxypropyltrimonium Hydrolyzed Wheat Protein (COGNIS)

42. Shampoo

| | |
|---|---|
| Texapon ® NSO | 43.0 |
| Dehyton ® K[27] | 10.0 |
| Plantacare ® 1200 UP[28] | 4.0 |
| Euperlan ® PK 3000[29] | 1.6 |
| Arquad ® 316[30] | 0.8 |
| Polymer JR ® 400 | 0.3 |
| Gluadin ® WQ | 4.0 |
| Glucamate ® DOE 120[31] | 0.5 |
| Dihydro-3-hydroxy-4,4-dimethyl-2(3H)-furanone | 0.5 |
| Sodium chloride | 0.2 |
| Water | ad 100 |

[27] INCI name: Cocamidopropyl Betaine ca. 30% active substance (COGNIS)
[28] C12–C16 fatty alcohol glycoside ca. 50% active substance (INCI name: Lauryl Glucoside) (COGNIS)
[29] Liquid disperion of pearlescence-imparting substances and amphoteric surfactant (ca. 62% active substance; CTFA name: Glycol Distearate (and) Glycerin (and) Laureth-4 (and) Cocoamidopropyl Betaine) (COGNIS)
[30] Tri-$C_{16}$-alkylmethylammonium chlordie (AKZO)
[31] Ethoxylated methyl glucoside dioleate (CFTA name: PEG-120 Methyl Glucose Dioleate) (AMERCHOL)

43. Shampoo

| | |
|---|---|
| Texapon ® N 70[32] | 21.0 |
| Plantacare ® 1200 UP | 8.0 |
| Gluadin ® WQ | 1.5 |
| Cutina ® EGMS[33] | 0.6 |
| Honeyquat ® 50[34] | 2.0 |
| Ajidew ® NL 50 | 2.8 |
| Antil ® 141[35] | 1.3 |
| Dihydro-3-hydroxy-4,4-dimethyl-2(3H)-furanone | 0.5 |
| Sodium chloride | 0.2 |
| Magnesium hydroxide | ad pH 4.5 |
| Water | ad 100 |

[32] Sodium lauryl ether sulfate with 2 mol of EO ca. 70% active substance (INCI name: Sodium Laureth Sulfate) (COGNIS)
[33] Ethylene glycol monostearate (ca. 25–35% monoester, 60–70% diester; INCI name: Glycol Stearate) (COGNIS)
[34] INCI name: Hydroxypropyltrimonium Honey (ca. 50% active substance) (BROOKS)
[35] Polyoxyethylene-propylene glycol dioleate (40% active substance; INCI name: Propylene Glycol (and) PEG-55 Propylene Glycol Oleate) (GOLDSCHMIDT)

44. Shampoo

| | |
|---|---|
| Texapon ® K 14 S[36] | 50.0 |
| Dehyton ® K | 10.0 |
| Plantacare ® 818 UP[37] | 4.5 |
| Polymer P1, corresponding to DE 39 29 973 | 0.6 |
| Cutina ® AGS[38] | 2.0 |
| D-Panthenol | 0.5 |
| Glucose | 1.0 |
| Dihydro-3-hydroxy-4,4-dimethyl-2(3H)-furanone | 0.5 |

-continued

| | |
|---|---|
| Salicyclic acid | 0.4 |
| Sodium chloride | 0.5 |
| Gluadin ® WQ | 2.0 |
| Water | ad 100 |

[36]Sodium lauryl myristyl ether sulfate ca. 28% active substance (INCI name: Sodium Myreth Sulfate) (COGNIS)
[37]C8–C16 fatty alcohol glycoside ca. 50% active substance (INCI name: Coco Glucoside) (COGNIS)
[38]Ethylene glycol stearate (ca. 5–15% monoester, 85–95% diester; INCI name: Glycol Distearate) (COGNIS)

45. Hair Treatment

| | |
|---|---|
| Celquat ® L 200[39] | 0.6 |
| Luviskol ® K30[40] | 0.2 |
| D-Panthenol | 0.5 |
| Polymer P1, corresponding to DE 39 29 973 | 0.6 |
| Dehyquart ® A-CA[41] | 1.0 |
| Gluadin ® W 40[42] | 1.0 |
| Natrosol ® 250 HR[43] | 1.1 |
| Dihydro-3-hydroxy-4,4-dimethyl-2(3H)-furanone | 0.5 |
| Gluadin ® WQ | 2.0 |
| Water | ad 100 |

[39]Quaternized cellulose derivative (95% active substance; CFTA name: Polyquaternium-4) (DELFT NATIONAL)
[40]Polyvinylpyrrolidone (95% active substance; CFTA name: PVP) (BASF)
[41]Cetyltrimethylammonium chloride (INCI name: Cetrimonium Chhloride) (COGNIS)
[42]Partial hydrolyzate from wheat ca. 40% active substance (INCI name: Hydrolyzed Wheat Gluten Hydrolyzed Wheat Protein) (COGNIS)
[43]Hydroxyethylcellulose (AQUALON)

46. Coloring Cream

| | |
|---|---|
| $C_{12-18}$-fatty alcohol | 1.2 |
| Lanette ® O[44] | 4.0 |
| Eumulgin ® B 2 | 0.8 |
| Cutina ® KD 16[45] | 2.0 |
| Sodium sulfite | 0.5 |
| L(+)-ascorbic acid | 0.5 |
| Ammonium sulfate | 0.5 |
| 1,2-Propylene glycol | 1.2 |
| Polymer JR ® 400 | 0.3 |
| p-Aminophenol | 0.35 |
| p-Tolylenediamine | 0.85 |
| 2-Methylresorcinol | 0.14 |
| 6-Methyl-m-aminophenol | 0.42 |
| Cetiol ® OE[46] | 0.5 |
| Dihydro-3-hydroxy-4,4-dimethyl-2(3H)-furanone | 0.5 |
| Honeyquat ® 50 | 1.0 |
| Ajidew ® NL 50 | 1.2 |
| Gluadin ® WQ | 1.0 |
| Ammonia | 1.5 |
| Water | ad 100 |

[44]Cetylstearyl alcohol (INCI name: Cetearyl Alcohol) (COGNIS)
[45]Self-emulsifying mixture of mono/diglycerides of higher saturated fatty acids with potassium stearate (INCI name: Glyceryl Stearate SE) (COGNIS)
[46]Di-n-octyl ether (INCI name: Dicaprylyl Ether) (COGNIS)

47. Developer Dispersion for Coloring Cream 12

| | |
|---|---|
| Texapon ® NSO | 2.1 |
| Hydrogen peroxide (50% strength) | 12.0 |
| Turpinal ® SL[47] | 1.7 |
| Latekoll ® D[48] | 12.0 |
| Dihydro-3-hydroxy-4,4-dimethyl-2(3H)-furanone | 0.5 |
| Gluadin ® WQ | 0.3 |

-continued

| | |
|---|---|
| Salcare ® SC 96 | 1.0 |
| Water | ad 100 |

[47]1-Hydroxyethane-1,1-diphosphonic acid (60% active substance; INCI name: Etidronic Acid) (COGNIS)
[48]Acrylic ester-methacrylic acid copolyer (25% active substance) (BASF)

The coloring cream had a pH of 10.0. It brought about an intensive red tinting of the hair.

48. Tinting Shampoo

| | |
|---|---|
| Texapon ® N 70 | 14.0 |
| Dehyton ® K | 10.0 |
| Akypo ® RLM 45 NV[49] | 14.7 |
| Plantacare ® 1200 UP | 4.0 |
| Polymer P1, corresponding to DE 39 29 973 | 0.3 |
| Cremophor ® RH 40[50] | 0.8 |
| Dye C.I. 12 719 | 0.02 |
| Dye C.I. 12 251 | 0.02 |
| Dye C.I. 12 250 | 0.04 |
| Dihydro-3-hydroxy-4,4-dimethyl-2(3H)-furanone | 0.5 |
| Dye C.I. 56 059 | 0.03 |
| Preservative | 0.25 |
| Perfume oil | q.s. |
| Eutanol ® G[51] | 0.3 |
| Gluadin ® WQ | 1.0 |
| Honeyquat ® 50 | 1.0 |
| Salcare ® SC 96 | 0.5 |
| Water | ad 100 |

[49]Lauryl alcohol + 4.5 ethylene oxide acetic acid sodium salt (20.4% active substance) (CHEM-Y)
[50]Castor oil, hydrogenated + 45 ethylene oxide (INCI name: PEG-40 Hydrogenated Castor Oil) (BASF)
[51]2-Octyldodecanol (Guerbet Alcohol) (INCI name: Octyldodecanol) (COGNIS)

Upon washing the hair with this tinting shampoo, the hair is given a glossy pale-blonde shade.

49. Cream Permanent Wave

| Waving cream | |
|---|---|
| Plantacare ® 810 UP[52] | 5.0 |
| Thioglycolic acid | 8.0 |
| Turpinal ® SL | 0.5 |
| Ammonia (25% strength) | 7.3 |
| Ammonium carbonate | 3.0 |
| Cetyl/stearyl alcohol | 5.0 |
| Guerbet Alcohol | 4.0 |
| Dihydro-3-hydroxy-4,4-dimethyl-2(3H)-furanone | 0.5 |
| Salcare ® SC 96 | 3.0 |
| Gluadin ® WQ | 2.0 |
| Perfume oil | q.s. |
| Water | ad 100 |

[52]$C_8$–$C_{10}$-Alkyl glucoside with degree of oligomerization 1.6 (ca. 60% active substance) (COGNIS)

| | |
|---|---|
| Plantacare ® 810 UP | 5.0 |
| Hydrogenated castor oil | 2.0 |
| Potassium bromate | 3.5 |
| Nitrilotriacetic acid | 0.3 |
| Citric acid | 0.2 |
| Dihydro-3-hydroxy-4,4-dimethyl-2(3H)-furanone | 0.5 |
| Merquat ® 550[53] | 0.5 |
| Hydagen ® HCMF[54] | 0.5 |
| Gluadin ® WQ | 0.5 |

-continued

| | | q.s. |
|---|---|---|
| Perfume oil | | q.s. |
| Water | | ad 100 |

[53] Dimethyldiallylammonium chloride-acrylamide copolymer (8% active substance; INCI name: Polyquarternium-7) (MOBIL OIL)
[54] Chitosan powder (INCI name: Chitosan) (COGNIS)

50. Face Tonics

| | 50.1 | 50.2 | 50.3 |
|---|---|---|---|
| Pluronic ® L 64[55] | 3.0 | 4.0 | 5.0 |
| Dihydro-3-hydroxy-4,4-dimethyl-2 (3H)-furanone | 0.25 | 0.25 | 0.25 |
| Dipropylene glycol | 10.0 | 10.0 | 10.0 |
| Emulsifier TD9/PEG40HCO[56] | 0.5 | 0.5 | 0.5 |
| Fragrance | 0.2 | 0.2 | 0.2 |
| Zn gluconate | 0.05 | 0.07 | 0.10 |
| Hydagen ® CMF[57] | 3.5 | 6.0 | 9.5 |
| Water (NaOH to pH = 5) | ad 100 | ad 100 | ad 100 |

[55] EO-PO-EO block polymer (EO = 40% by weight), OH number = 39.1
[56] Trideceth 9 and PEG40-hydrogenated castor oil
[57] Solution of chitosan (ca. 1% by weight) in a 0.4% strength aqueous glycolic acid solution 51. Hydrogels

| | 51.1 | 51.2 |
|---|---|---|
| Pluronic ® L64 | 3.0 | 3.0 |
| Methocel ® E4M[58] | 0.3 | 0.20 |
| Dihydro-3-hydroxy-4,4-dimethyl-2(3H)-furanone | 0.25 | 0.25 |
| Dipropylene glycol | 10.0 | 10.0 |
| Emulsifier TD9/PEG40HCO | 0.5 | 0.50 |
| Fragrance | 0.2 | 0.20 |
| Zn gluconate | 0.05 | 0.10 |
| Hydagen ® CMF | 3.5 | 8.0 |
| Water (NaOH to pH = 5) | ad 100 | ad 100 |

[58] Methylhydroxypropylcellulose (DOW)

52. Skin Emulsions (O/W)

| | 52.1 | 52.2 |
|---|---|---|
| Emulgade ® SE[59] | 8.0 | 8.0 |
| Cutina ® MD-A[60] | 1.5 | 1.5 |
| Cetyl/stearyl alcohol | 1.5 | 1.5 |
| Myritol ® 318[61] | 10.0 | 10.0 |
| 2-Ethylhexyl stearate | 5.0 | 5.0 |
| Dimethylpolysiloxane (350 at) | 1.0 | 1.0 |
| Controx ® KS[62] | 0.05 | 0.05 |
| PHB propyl ester | 0.2 | 0.2 |
| PHB methyl ester | 0.2 | 0.2 |
| Dihydro-3-hydroxy-4,4-dimethyl-2(3H)-furanone | 0.5 | 0.25 |
| 1,2-Propylene glycol | 3.0 | 3.0 |
| Hydagen ® CMF | 3.0 | 8.0 |
| Zn gluconate | 0.04 | 0.10 |
| Water (NaOH to pH = 5) | ad 100 | ad 100 |

[59] Mixture of: glyceryl stearate, ceteareth-20, ceteareth-12, cetearyl alcohol and cetylpalmitate (COGNIS)
[60] Glyceryl stearate (COGNIS)
[61] Caprylic/capric triglyceride (COGNIS)
[62] Tocopherol and hydrogenated tallow glycerides citrate (COGNIS)

What is claimed is:

1. A cosmetic agent comprising a 2-furanone derivative of the formula (I) and/or of the formula (II):

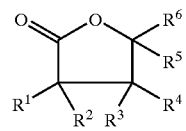

formula (I)

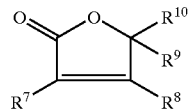

formula (II)

wherein the radicals $R^1$ to $R^{10}$, independently of one another, are selected from the group consisting of
hydrogen, —OH, a methyl, methoxy, an aminomethyl or hydroxymethyl radical,
a —$C_2$–$C_4$-saturated or mono- or diunsaturated, branched or linear hydrocarbon radical,
a —$C_2$–$C_4$-saturated or mono- or diunsaturated, branched or linear mono-, di- or trihydroxy hydrocarbon radical,
a —$C_2$–$C_4$-saturated or mono- or diunsaturated, branched or linear mono-, di- or triamino hydrocarbon radical, a group —$OR^{11}$, where $R^{11}$ is selected from a —$C_2$–$C_4$-saturated or mono- or diunsaturated, branched or linear hydrocarbon radical, a —$C_2$–$C_4$-saturated or mono- or diunsaturated, branched or a linear mono-, di- or trihydroxy hydrocarbon radical,
a group —$NR^{12}R^{13}$, where $R^{12}$ and $R^{13}$ independently of one another, are selected from hydrogen, methyl, a —$C_2$–$C_4$-saturated or mono- or diunsaturated, branched or linear hydrocarbon radical or a —$C_2$–$C_4$-saturated or mono- or diunsaturated, branched or linear mono-, di- or trihydroxy hydrocarbon radical,
a group —$COOR^{14}$, where $R^{14}$ is selected from hydrogen, methyl, a —$C_2$–$C_4$-saturated or mono- or diunsaturated, branched or linear hydrocarbon radical, a —$C_2$–$C_4$-saturated mono- or diunsaturated, branched or linear mono-, di- or trihydroxy hydrocarbon radical or a —$C_2$–$C_4$-saturated or mono- or diunsaturated, branched or linear mono-, di- or triamino hydrocarbon radical,
a group —$CONR^{15}R^{16}$, where $R^{15}$ and $R^{16}$ are independently selected from hydrogen, methyl, a —$C_2$–$C_4$-saturated or mono- or diunsaturated, branched or linear hydrocarbon radical, a —$C_2$–$C_4$-saturated mono- or diunsaturated, branched or linear mono-, di- or trihydroxy hydrocarbon radical or a —$C_2$–$C_4$-saturated or mono- or diunsaturated, branched or linear mono-, di- or triamino hydrocarbon radical,
a group —$COR^{16}$, where $R^{16}$ is selected from methyl, a —$C_2$–$C_4$-saturated or mono- or diunsaturated, branched or linear hydrocarbon radical, a —$C_2$–$C_4$-saturated or mono- or diunsaturated, branched or linear mono-, di- or trihydroxy hydrocarbon radical or a —$C_2$–$C_4$-saturated or mono- or diunsaturated, branched or linear mono-, di- or triamino hydrocarbon radical, and
a group —$OCOR^{17}$, where $R^{17}$ is methyl, a —$C_2$–$C_{30}$-saturated or mono- or polyunsaturated, branched or linear hydrocarbon radical, a —$C_2$–$C_{30}$-saturated or mono- or polyunsaturated, branched or linear mono-, di-, tri- or polyhydroxy hydrocarbon radical or a —$C_2$–$C_{30}$-saturated or mono- or polyunsaturated, branched or linear mono-, di-, tri- or polyamino hydrocarbon radical, with the proviso that when $R^7$ and $R^8$ are —OH and $R^9$ or $R^{10}$ are hydrogen, the remaining groups $R^9$ and $R^{10}$ are not a dihydroxyethyl radical.

2. The cosmetic agent of claim 1, wherein $R^1$, $R^2$ and $R^7$, independently are selected from the group consisting of:

hydrogen, —OH, methyl, methoxy, aminomethyl, hydroxymethyl, a —$C_2$–$C_4$-saturated or mono- or diunsaturated, branched or linear mono-, di- or trihydroxy hydrocarbon radical, a —$C_2$–$C_4$-saturated or mono- or diunsaturated, branched or linear mono-, di- or triamino hydrocarbon radical, a group —$OR^{11}$, where $R^{11}$ is selected from a —$C_2$–$C_4$-saturated or mono- or diunsaturated, branched or linear hydrocarbon radical or a —$C_2$–$C_4$-saturated or mono- or diunsaturated, branched or linear mono-, di- or trihydroxy hydrocarbon radical, a group —$COOR^{14}$, where $R^{14}$ is selected from hydrogen, methyl, a —$C_2$–$C_4$-saturated or mono- or diunsaturated, branched or linear hydrocarbon radical, a —$C_2$–$C_4$-saturated or mono- or diunsaturated, branched or linear mono-, di- or trihydroxy hydrocarbon radical or a —$C_2$–$C_4$-saturated or mono- or diunsaturated, branched or linear mono-, di- or triamino hydrocarbon radical, a group —$COR^{16}$, where $R^{16}$ is selected from a methyl, a —$C_2$–$C_4$-saturated or mono- or diunsaturated, branched or linear hydrocarbon radical, a —$C_2$–$C_4$-saturated or mono- or diunsaturated, branched or linear mono-, di- or trihydroxy hydrocarbon radical or a —$C_2$–$C_4$-saturated or mono- or diunsaturated, branched or linear mono-, di- or triamino hydrocarbon radical, and a group —$OCOR^{17}$, where $R^{17}$ is selected from methyl, a —$C_2$–$C_{30}$-saturated or mono- or polyunsaturated, branched or linear hydrocarbon radical, a —$C_2$–$C_{30}$-saturated or mono- or polyunsaturated, branched or linear mono-, di-, tri- or polyhydroxyalkyl radical or a —$C_2$–$C_{30}$-saturated or mono- or polyunsaturated, branched or linear mono-, di-, tri- or polyaminohydrocarbon radical.

3. The cosmetic agent of claim 2, wherein $R^3$, $R^4$ and $R^8$, independently are selected from the group consisting of:

hydrogen, —OH, methyl, methoxy, aminomethyl, hydroxymethyl, a —$C_2$–$C_4$-saturated or mono- or diunsaturated, branched or linear hydrocarbon radical, a —$C_2$–$C_4$-saturated or mono- or diunsaturated, branched or linear mono-, di- or trihydroxy hydrocarbon radical and a —$C_2$–$C_4$-saturated or mono- or diunsaturated, branched or linear mono-, di- or triamino hydrocarbon radical.

4. The cosmetic agent of claim 3 wherein $R^5$, $R^6$, $R^9$ and $R^{10}$, independently are selected from the group consisting of:

hydrogen, —OH, methyl, methoxy, aminomethyl, hydroxymethyl, a —$C_2$–$C_4$-saturated or mono- or diunsaturated, branched or linear hydrocarbon radical, a —$C_2$–$C_4$-saturated or mono- or diunsaturated, branched or linear mono-, di- or trihydroxy hydrocarbon radical and a —$C_2$–$C_4$-saturated or mono- or diunsaturated, branched or linear mono-, di- or triamino hydrocarbon radical.

5. The cosmetic agent of claim 4 wherein the 2-furanone derivative has the formula (I).

6. The cosmetic agent as claimed in claim 5, wherein $R^1$ and $R^2$, independently are selected from the group consisting of:

hydrogen, —OH, methyl, methoxy, aminomethyl, hydroxymethyl, a —$C_2$–$C_4$-saturated or mono- or diunsaturated, branched or linear mono-, di- or trihydroxy hydrocarbon radical, a group —$OR^{11}$, where $R^{11}$ is selected from a —$C_2$–$C_4$-saturated or mono- or diunsaturated, branched or linear hydrocarbon radical or a —$C_2$–$C_4$-saturated or mono- or diunsaturated, branched or linear mono-, di- or trihydroxy hydrocarbon radical, a group —$COOR^{14}$, where $R^{14}$ is selected from hydrogen, methyl, a —$C_2$–$C_4$-saturated or mono- or diunsaturated, branched or linear hydrocarbon radical or a —$C_2$–$C_4$-saturated mono- or diunsaturated, branched or linear mono-, di- or trihydroxy hydrocarbon radical, a group —$COR^{16}$, where $R^{16}$ is selected from methyl, a —$C_2$–$C_4$-saturated or mono- or diunsaturated, branched or linear hydrocarbon radical or a —$C_2$–$C_4$-saturated or mono- or diunsaturated, branched or linear mono-, di- or trihydroxy hydrocarbon radical, and a group —$OCOR^{17}$, where $R^{17}$ is selected from methyl, a —$C_2$–$C_{30}$-saturated and/or mono- or polyunsaturated, branched or linear hydrocarbon radical or a —$C_2$–$C_{30}$-saturated or mono- or polyunsaturated, branched or linear mono-, di-, tri- or polyhydroxy hydrocarbon radical.

7. The cosmetic agent of claim 6, wherein $R^3$ and $R^4$, independently are selected from the group consisting of:

hydrogen, —OH, methyl, methoxy, aminomethyl, hydroxymethyl, a —$C_2$–$C_4$-saturated or mono- or diunsaturated, branched or linear mono-, di- or trihydroxy hydrocarbon radical, a group —$OR^{11}$, where $R^{11}$ is selected from a —$C_2$–$C_4$-saturated or mono- or diunsaturated, branched or linear hydrocarbon radical or a —$C_2$–$C_4$-saturated or mono- or diunsaturated, branched or linear mono-, di- or trihydroxy hydrocarbon radical, a group —$COOR^{14}$, where $R^{14}$ is selected from hydrogen, methyl, a —$C_2$–$C_4$-saturated or mono- or diunsaturated, branched or linear hydrocarbon radical or a —$C_2$–$C_4$-saturated mono- or diunsaturated, branched or linear mono-, di- or trihydroxy hydrocarbon radical, and a group —$OCOR^{17}$, where $R^{17}$ is selected from methyl, a —$C_2$–$C_{30}$-saturated or mono- or polyunsaturated, branched or linear hydrocarbon radical or a —$C_2$–$C_{30}$-saturated or mono- or polyunsaturated, branched or linear mono-, di-, tri- or polyhydroxy hydrocarbon radical.

8. The cosmetic agent of claim 7, wherein $R^5$ and $R^6$, independently are selected from the group consisting of:

hydrogen, —OH, methyl, methoxy, aminomethyl, hydroxymethyl, a —$C_2$–$C_4$-saturated or mono- or diunsaturated, branched or linear mono-, di- or trihydroxy hydrocarbon radical, and a group —$OR^{11}$, where $R^{11}$ is selected from a —$C_2$–$C_4$-saturated or mono- or diunsaturated, branched or linear hydrocarbon radical or a —$C_2$–$C_4$-saturated or mono- or diunsaturated, branched or linear mono-, di- or trihydroxy hydrocarbon radical.

9. The cosmetic agent of claim 8, wherein the compound of formula (I) is dihydro-3-hydroxy-4,4-dimethyl-2(3H)-furanone.

10. The cosmetic agent of claim 9 which in addition contains a polymer.

11. The cosmetic agent of claim 10 which in addition contains a protein hydrolyzate and/or derivative thereof.

12. The cosmetic agent of claim 11 which in addition contains a surfactant.

13. The cosmetic agent of claim 12 which in addition contains an emulsifier.

14. The cosmetic agent of claim 13 which in addition contains a solid fatty substance.

15. The cosmetic agent of claim 14 which in addition contains a vitamin, a provitamin, a vitamin precursor or derivatives thereof.

16. The cosmetic agent of claim 15 which in addition contains a substance which contains primary or secondary amino groups.

17. A method of treating human or animal skin comprising applying to said skin the cosmetic agent of claim 1.

* * * * *